(12) United States Patent
Cordingley, V et al.

(10) Patent No.: US 8,653,078 B2
(45) Date of Patent: Feb. 18, 2014

(54) HERBICIDAL PYRIDO[2,3-B]PYRAZINES

(71) Applicant: Syngenta Limited, Guildford (GB)

(72) Inventors: Matthew Robert Cordingley, V, Fulbourn (GB); Michael Drysdale Turnbull, Bracknell (GB); Neil Brian Carter, Bracknell (GB); Patrick Jelf Crowley, Crowthorne (GB)

(73) Assignee: Syngenta Limited, Guildford, Surrey ( * ) Notice: Subject to any disclaimer, the term of this patent is extended or adjusted under 35 U.S.C. 154(b) by 0 days.

(21) Appl. No.: 13/723,270

(22) Filed: Dec. 21, 2012

(65) Prior Publication Data

US 2013/0137574 A1 May 30, 2013

Related U.S. Application Data

(62) Division of application No. 12/863,286, filed as application No. PCT/GB2009/000127 on Jan. 16, 2009, now Pat. No. 8,338,598.

(30) Foreign Application Priority Data

Jan. 17, 2008 (GB) .................... 0800856.7

(51) Int. Cl.
*A61K 31/495* (2006.01)
(52) U.S. Cl.
USPC .......................................... 514/249; 544/350
(58) Field of Classification Search
USPC .......................................... 514/249; 544/350
See application file for complete search history.

(56) References Cited

FOREIGN PATENT DOCUMENTS

| WO | 03/010145 | 2/2003 |
|---|---|---|
| WO | 2004/056825 | 7/2004 |
| WO | 2005/123733 | 12/2005 |

*Primary Examiner* — Douglas M Willis
(74) *Attorney, Agent, or Firm* — James Cueva

(57) ABSTRACT

The present invention relates to a method of controlling plants or inhibiting plant growth which comprises applying to the plants or to the locus thereof a herbicidally effective amount of a compound of formula (I)

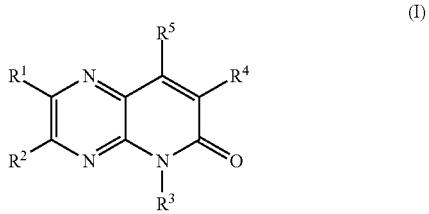

wherein $R^1$, $R^2$, $R^3$, $R^4$ and $R^5$ are as defined in claim 1; or a salt or N-oxide thereof.

Furthermore, the present invention relates to processes for preparing compounds of formula (I), to intermediates used in the preparation of compounds of formula (I), to herbicidal compositions comprising compounds of formula (I) and to certain novel pyridopyridines.

4 Claims, No Drawings

HERBICIDAL PYRIDO[2,3-B]PYRAZINES

CROSS REFERENCE TO RELATED APPLICATIONS

This application is a divisional of U.S. application Ser. No. 12/863,286, filed on Jul. 16, 2010, which is a U.S. National Stage under 35 U.S.C. §371 of International Application No. PCT/GB2009/000127 filed Jan. 16, 2009, which claims priority to GB 0800856.7 filed Jan. 17, 2008, the contents of which are incorporated herein by reference the contents of which are incorporated herein by reference.

DESCRIPTION

The present invention relates to novel herbicidal pyrido[2,3-b]pyrazines, to processes for their preparation, to compositions comprising these compounds, and to their use in controlling plants or in inhibiting plant growth.

Pyrido[2,3-b]pyrazines were disclosed as intermediates in the synthesis of fungicidal compounds, for example, in WO 04/056825, WO 05/123698 and WO 05/123733. Pyrido[2,3-b]pyrazines were disclosed as fungicidal compounds in WO 05/010000.

It has now surprisingly been found that certain pyrido[2,3-b]pyrazines display excellent herbicidal and growth-inhibiting properties.

The present invention therefore provides a method of controlling plants which comprises applying to the plants or to the locus thereof a herbicidally effective amount of a compound of formula (I)

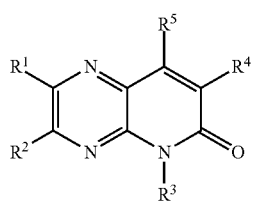

(I)

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different;
$R^4$ is heteroaryl or heteroaryl substituted by one to four $R^8$, which may be the same or different;
$R^5$ is hydroxy or a group which can be metabolised to a hydroxy group;
each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

For example, a compound of formula (Ia), i.e. a compound of formula (I) wherein $R^3$ is hydrogen and $R^5$ is hydroxy, can be drawn in at least five tautomeric forms.

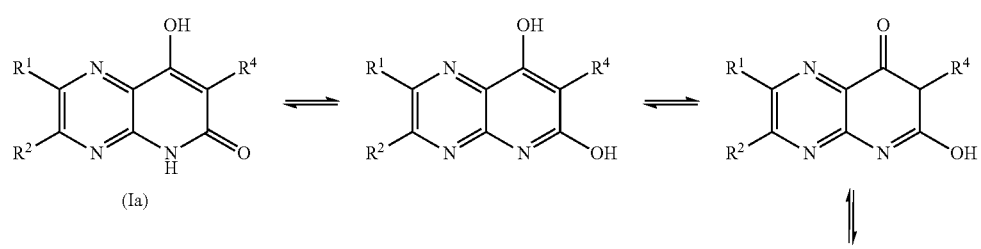

(Ia)

-continued

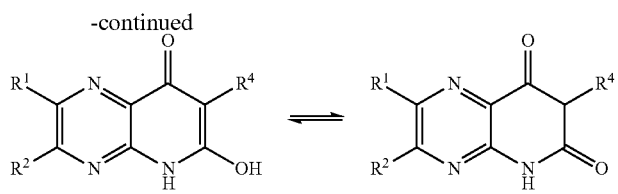

Some of these compounds exhibit good herbicidal activity. Additionally, these compounds can be used as intermediates for the synthesis of compounds of the formula (Ib), (Ic) and (Id).

For example, a compound of formula (Ib), i.e. a compound of formula (I) wherein $R^3$ is hydrogen and $R^5$ is as defined for compounds of formula (I) other than hydroxy, can be drawn in at least two tautomeric forms.

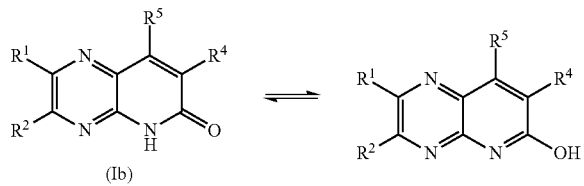

(Ib)

Some of these compounds exhibit good herbicidal activity. Additionally, these compounds can be used as intermediates for the synthesis of compounds of the formula (Ia), (Ic) and (Id).

A compound of formula (Ic), i.e. a compound of formula (I) wherein $R^3$ is as defined for compounds of formula (I) other than hydrogen and $R^5$ is as defined for compounds of formula (I) other than hydroxy, can be drawn in only one tautomeric form.

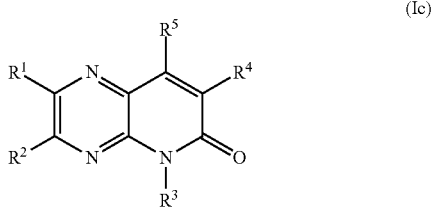

(Ic)

Most of these compounds exhibit excellent herbicidal activity. Additionally, these compounds can be used as intermediates for the synthesis of compounds of the formula (Ia), (Ib) and (Id).

A compound of formula (Id), i.e. a compound of formula (I) wherein $R^3$ is as defined for compounds of formula (I) other than hydrogen and $R^5$ is hydroxy, can be drawn in three tautomeric forms.

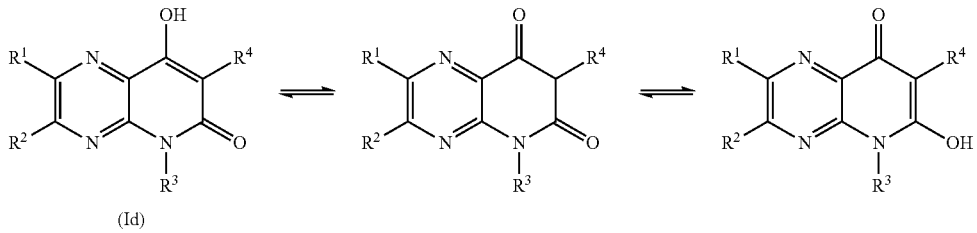

(Id)

Most of these compounds exhibit good herbicidal activity. Additionally, these compounds can be used as intermediates for the synthesis of compounds of the formula (Ia), (Ib) and (Ic).

Each alkyl moiety (either alone or as part of a larger group, such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl, prop-2-enyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CHF_2$, —$CH_2CF_3$ or —$CH_2CHF_2$. Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CF=$CH_2$ or —C≡CCl.

Cyanoalkyl groups are alkyl groups which are substituted with one or more cyano groups, for example, cyanomethyl or 1,3-dicyanopropyl.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings contain up to three and bicyclic systems up to four heteroatoms which are preferably chosen from nitrogen, oxygen and sulfur. Examples of monocyclic groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. More preferred monocyclic groups are pyridyl, pyrimidinyl, thiophenyl, isoxazolyl, oxadiazolyl, and thiazolyl. Examples of bicyclic groups are benzothiophenyl, benzimidazolyl, benzothiadiazolyl, quinolinyl, isoquinolinyl, cinnolinyl, quinoxalinyl and pyrazolo[1,5-a]pyrimidinyl. More preferred bicyclic groups are quinolinyl and isoquinolinyl.

The term "heterocyclyl" is defined to include heteroaryl and in addition their unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation. The term "metabolism" as used herein means the conversion or breakdown of a substance from one form to another by a living organism, in particular in a plant (in planta).

Preferred values of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are, in any combination, as set out below.

Preferably $R^1$ is hydrogen, $C_1$-$C_4$alkyl, $C_1$-$C_4$haloalkyl, halo, cyano, hydroxy or $C_1$-$C_4$alkoxy.

More preferably $R^1$ is hydrogen, $C_1$-$C_4$alkyl, halo, cyano or hydroxy.

Even more preferably $R^1$ is hydrogen, methyl, chloro or bromo.

Yet even more preferably $R^1$ is hydrogen or chloro.

Most preferably $R^1$ is hydrogen.

Preferably $R^2$ is hydrogen, $C_1$-$C_4$alkyl, $C_1$-$C_4$haloalkyl, halo, cyano, hydroxy or $C_1$-$C_4$alkoxy.

More preferably $R^2$ is hydrogen, $C_1$-$C_4$alkyl, halo, cyano or hydroxy.

Even more preferably $R^2$ is hydrogen, methyl, chloro or bromo.

Yet even more preferably $R^2$ is hydrogen or chloro.

Most preferably $R^2$ is hydrogen.

Preferably $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl. Examples of such preferred groups for $R^3$ are hydrogen, methyl, ethyl, n-propyl, iso-propyl, n-butyl, 2-methyl-propyl, 2-fluoro-ethyl, 2,2-difluoro-ethyl, 2,2,2-trifluoro-ethyl, allyl, but-3-en-1-yl or propargyl.

More preferably $R^3$ is hydrogen, $C_1$-$C_2$alkyl, $C_1$-$C_2$haloalkyl, $C_2$-$C_3$alkenyl or $C_2$-$C_3$alkynyl. Examples of such more preferred groups for $R^3$ are hydrogen, methyl, ethyl, 2,2-difluoro-ethyl, 2,2,2-trifluoro-ethyl, allyl or propargyl.

Most preferably $R^3$ is hydrogen, $C_1$-$C_2$alkyl, $C_1$-$C_2$haloalkyl or $C_2$-$C_3$alkynyl. Examples of such most preferred groups for $R^3$ are hydrogen, methyl, ethyl, 2,2-difluoro-ethyl or propargyl.

Preferably $R^4$ is heteroaryl substituted by one to three $R^8$, which may be the same or different.

More preferably $R^4$ is a monocyclic heteroaryl, containing up to two heteroatoms, substituted by one to three $R^8$, which may be the same or different, or $R^4$ is a bicyclic heteroaryl, containing up to three heteroatoms, substituted by one to three $R^8$, which may be the same or different.

Even more preferably $R^4$ is pyridyl, pyrimidinyl, thiophenyl, isoxazolyl, oxadiazolyl, or thiazolyl, substituted by one to three $R^8$, which may be the same or different, or $R^4$ is quinolinyl or isoquinolinyl, substituted by one to three $R^8$, which may be the same or different. Examples of such most preferred groups for $R^4$ include 3,5-dichloro-pyrid-2-yl, 3,5-dichloro-pyrid-4-yl, 2,6-dichloro-pyrid-3-yl, 2,4-dichloro-pyrid-3-yl, 4,6-dichloro-pyrid-3-yl, 2,5-dichloro-pyrid-4-yl, 3,6-dichloro-pyrid-2-yl, 3-chloro-5-fluoro-pyrid-2-yl, 3-chloro-5-trifluoromethyl-pyrid-2-yl, 3,5,6-trichloro-pyrid-2-yl, 2,5-dichloro-pyrid-3-yl, 2,3-dichloro-pyrid-4-yl, 2-chloro-4-trifluoromethyl-pyrid-3-yl, 2-chloro-6-trifluoromethyl-pyrid-3-yl, 3-chloro-5-trifluoromethyl-pyrid-4-yl, 2,3,5-trichloro-pyrid-4-yl, 5-chloro-pyrimidin-4-yl, 3,4,5-trichloro-thiophen-2-yl, 2,5-dichloro-thiophen-3-yl, 3-trifluoromethyl-isoxazol-5-yl, 3-trifluoromethyl-4-chloro-isoxazol-5-yl, 3,4-dichloro-isoxazol-5-yl, 3-methyl-1,2,4-oxadiazol-5-yl, 3-trifluoromethyl-1,2,4-oxadiazol-5-yl, 2,4-dichloro-thiazol-5-yl, 2-chloro-4-methyl-thiazol-5-yl, 2,5-dichloro-thiazol-4-yl, 2,4-dichloro-quinolin-3-yl, 4-chloro-2-trifluoromethyl-quinolin-3-yl, 1-chloro-isoquinolin-3-yl, and 1,4-dichloro-isoquinolin-3-yl.

In one preferred embodiment $R^4$ is 3,5-dichloro-pyrid-2-yl.

In one preferred embodiment $R^4$ is 3,5-dichloro-pyrid-4-yl.

In one preferred embodiment $R^4$ is 2,6-dichloro-pyrid-3-yl.

In one preferred embodiment $R^4$ is 2,4-dichloro-pyrid-3-yl.

In one preferred embodiment $R^4$ is 4,6-dichloro-pyrid-3-yl.

In one preferred embodiment $R^4$ is 2,5-dichloro-pyrid-4-yl.

In one preferred embodiment $R^4$ is 3-trifluoromethyl-isoxazol-5-yl.

In one preferred embodiment $R^4$ is 3-methyl-1,2,4-oxadiazol-5-yl.

In one preferred embodiment $R^4$ is 2-chloro-4-methyl-thiazol-5-yl.

Preferably $R^5$ is hydroxy, $R^9$-oxy-, $R^{10}$-carbonyloxy-, tri-$R^{11}$-silyloxy- or $R^{12}$-sulfonyloxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;

$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different;

each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy.

More preferably $R^5$ is hydroxy, $R^9$-oxy- or $R^{10}$-carbonyloxy-.

Even more preferably $R^5$ is hydroxy, $C_1$-$C_4$alkoxy, $C_1$-$C_4$alkenyloxy, $C_4$alkynyloxy, aryl-$C_1$-$C_4$alkoxy or aryl-$C_1$-$C_4$alkoxy wherein the aryl moiety is substituted by one to three $R^{14}$, which may be the same or different, heteroaryl-$C_1$-$C_4$alkoxy or heteroaryl-$C_1$-$C_4$alkoxy wherein the heteroaryl moiety is substituted by one to three $R^{14}$, which may be the same or different, $C_1$-$C_4$alkylcarbonyloxy-, $C_3$-$C_6$cycloalkylcarbonyloxy-, $C_3$-$C_{10}$cycloalkyl-$C_1$-$C_{10}$alkylcarbonyloxy-, $C_1$-$C_4$haloalkylcarbonyl-oxy-, $C_2$-$C_4$alkenylcarbonyloxy-, $C_2$-$C_4$alkynylcarbonyloxy-, $C_1$-$C_4$alkoxy-$C_1$-$C_4$alkyl-carbonyloxy-, $C_1$-$C_4$alkylthio-$C_1$-$C_4$alkylcarbonyloxy-, $C_1$-$C_4$alkoxycarbonyloxy-, $C_2$-$C_4$alkenyloxycarbonyloxy-, $C_2$-$C_4$alkynyloxycarbonyloxy-, $C_1$-$C_4$alkylthiocarbonyloxy-, N—$C_1$-$C_4$alkyl-aminocarbonyloxy-, N,N-di-($C_1$-$C_4$alkyl)-aminocarbonyloxy-, aryl-carbonyloxy- or arylcarbonyloxy-substituted by one to three $R^{14}$, which may be the same or different, heteroarylcarbonyloxy- or heteroarylcarbonyloxy-substituted by one to three $R^{14}$, which may be the same or different, aryl-$C_1$-$C_4$alkylcarbonyloxy- or aryl-$C_1$-$C_4$alkylcarbonyloxy- wherein the aryl moiety is substituted by one to three $R^{14}$ which may be the same or different, heteroaryl-$C_1$-$C_4$alkylcarbonyloxy- or heteroaryl-$C_1$-$C_4$alkylcarbonyloxy- wherein the heteroaryl moiety is substituted by one to three $R^{14}$, which may be the same or different, aryloxycarbonyloxy- or aryloxycarbonyloxy-substituted by one to three $R^{14}$, which may be the same or different, heteroaryloxycarbonyloxy- or heteroaryloxycarbonyloxy-substituted by one to three $R^{14}$, which may be the same or different, arylthiocarbonyloxy- or arylthiocarbonyloxy-substituted by one to three $R^{14}$, which may be the same or different, or heteroarylthiocarbonyloxy- or heteroarylthiocarbonyloxy-substituted by one to three $R^{14}$, which may be the same or different. Examples of preferred groups for $R^5$ are hydroxy, methoxy, ethoxy, allyloxy, propargyloxy, benzyloxy, methylcarbonyloxy-, ethylcarbonyloxy-, iso-propylcarbonyloxy-, n-propylcarbonyloxy-, but-2-ylcarbonyloxy-, 2-methyl-propylcarbonyloxy-, tert-butylcarbonyloxy-, cyclopropylcarbonyloxy-, cyclopentyl-methylcarbonyloxy-, chloromethylcarbonyloxy-, trifluoromethylcarbonyloxy-, allylcarbonyloxy-, (E)-prop-1-en-1-ylcarbonyloxy-, 2-methyl-prop-1-en-1-ylcarbonyloxy-, methoxymethylcarbonyl-oxy-, ethoxycarbonyloxy-, tert-butoxycarbonyloxy-, but-2-yn-1-yloxycarbonyloxy-, ethylthiocarbonyloxy-, N,N-diethylaminocarbonyloxy-, phenylcarbonyloxy-, 3-methoxy-phenylcarbonyloxy-, 4-nitro-phenylcarbonyloxy-, benzylcarbonyloxy-, furan-2-ylcarbonyloxy-, 2,5-dimethyl-furan-3-ylcarbonyloxy-, thiophen-2-ylcarbonyloxy-, 3,5-dimethyl-isoxazol-4-ylcarbonyloxy-, and 1-phenyl-prop-1-ylcarbonyloxy-.

Yet even more preferably $R^5$ is hydroxy, $C_1$-$C_4$alkylcarbonyloxy-, $C_3$-$C_6$cyclo-alkylcarbonyloxy-, $C_2$-$C_4$alkenylcarbonyloxy-, $C_2$-$C_4$alkynylcarbonyloxy-, $C_1$-$C_4$alkoxycarbonyloxy-, $C_2$-$C_4$alkenyloxycarbonyloxy-, $C_2$-$C_4$alkynyloxycarbonyloxy- or $C_1$-$C_4$alkylthiocarbonyloxy-. Examples of more preferred groups for $R^5$ are hydroxy, methylcarbonyloxy-, ethylcarbonyloxy-, iso-propylcarbonyloxy-, n-propylcarbonyloxy-, but-2-ylcarbonyloxy-, 2-methyl-propylcarbonyloxy-, tert-butylcarbonyloxy-, cyclopropylcarbonyloxy-, allylcarbonyloxy-, (E)-prop-1-en-1-ylcarbonyloxy-, 2-methyl-prop-1-en-1-ylcarbonyloxy-, ethoxycarbonyloxy-, tert-butoxycarbonyloxy-, but-2-yn-1-yloxycarbonyloxy-, and ethylthiocarbonyloxy-.

Most preferably $R^5$ is hydroxy, $C_1$-$C_4$alkylcarbonyloxy-, $C_1$-$C_4$alkoxycarbonyl-oxy- or $C_1$-$C_4$alkylthiocarbonyloxy-. Examples of most preferred groups for $R^5$ are hydroxy, methylcarbonyloxy-, ethylcarbonyloxy-, iso-propylcarbonyloxy-, n-propylcarbonyloxy-, but-2-ylcarbonyloxy-, 2-methyl-propylcarbonyloxy-, tert-butylcarbonyl-oxy-, ethoxycarbonyloxy-, and ethylthiocarbonyloxy-.

In one preferred embodiment $R^5$ is hydroxy.

In one preferred embodiment $R^5$ is $R^9$-oxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is $R^{10}$-carbonyloxy-, wherein $R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-

$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is iso-propylcarbonyloxy- or tert-butyl-carbonyloxy-.

Preferably each $R^6$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^6$ are chloro, fluoro, methyl, ethyl, trifluoromethyl, methoxy or trifluoromethoxy.

Preferably each $R^7$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^7$ are chloro, fluoro, methyl, ethyl, trifluoromethyl, methoxy and trifluoromethoxy.

Most preferably each $R^7$ is independently halo, $C_1$-$C_4$alkyl, $C_1$-$C_4$haloalkyl or $C_1$-$C_4$alkoxy. Examples of such preferred groups for $R^7$ are chloro, fluoro, methyl, ethyl, trifluoromethyl and methoxy.

Preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl- or $C_1$-$C_4$haloalkylsulfonyl-.

More preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$haloalkoxy, $C_1$-$C_{10}$alkylthio or $C_1$-$C_4$haloalkylthio. Examples of such more preferred groups for $R^8$ are iodo, bromo, chloro, fluoro, cyano, nitro, methyl, ethyl, trifluoromethyl, methoxy, trifluoromethoxy or trifluoromethylthio.

Even more preferably each $R^8$ is independently halo, $C_1$-$C_{10}$alkyl, $C_1$-$C_4$haloalkyl, $C_1$-$C_{10}$alkoxy or $C_1$-$C_4$haloalkoxy. Examples of such even more preferred groups for $R^8$ are bromo, chloro, fluoro, methyl, ethyl, trifluoromethyl, methoxy or trifluoromethoxy.

Even more preferably each $R^8$ is independently halo, $C_1$-$C_{10}$alkyl, or $C_1$-$C_4$haloalkyl. Examples of such even more preferred groups for $R^8$ are chloro, fluoro, methyl, or trifluoromethyl.

Preferably $R^9$ is $C_2$-$C_{10}$alkenyl, $C_2$-$C_{10}$alkynyl, aryl-$C_1$-$C_4$alkyl- or aryl-$C_1$-$C_4$alkyl- wherein the aryl moiety is substituted by one to three $R^{13}$, which may be the same or different.

More preferably $R^9$ is $C_3$-$C_4$alkenyl, or $C_3$-$C_4$alkynyl, benzyl or benzyl wherein the phenyl moiety is substituted by one to three $R^{13}$, which may be the same or different.

Even more preferably $R^9$ is allyl, propargyl or benzyl.

Most preferably $R^9$ is allyl.

Preferably $R^{10}$ is $C_1$-$C_4$alkyl, $C_3$-$C_6$cycloalkyl, $C_3$-$C_{10}$cycloalkyl-$C_1$-$C_{10}$alkyl, $C_1$-$C_4$haloalkyl, $C_2$-$C_4$alkenyl, $C_2$-$C_4$alkynyl, $C_1$-$C_4$alkoxy-$C_1$-$C_4$alkyl, $C_1$-$C_4$alkylthio-$C_1$-$C_4$alkyl, $C_1$-$C_4$alkoxy, $C_2$-$C_4$alkenyloxy, $C_2$-$C_4$alkynyloxy, $C_1$-$C_4$alkylthio, N—$C_1$-$C_4$alkyl-amino, N,N-di-($C_1$-$C_4$alkyl)-amino, aryl or aryl substituted by one to three $R^{14}$, which may be the same or different, heteroaryl or heteroaryl substituted by one to three $R^{14}$, which may be the same or different, aryl-$C_1$-$C_4$alkyl or aryl-$C_1$-$C_4$alkyl wherein the aryl moiety is substituted by one to three $R^{14}$, which may be the same or different, heteroaryl-$C_1$-$C_4$alkyl or heteroaryl-$C_1$-$C_4$alkyl wherein the heteroaryl moiety is substituted by one to three $R^{14}$, which may be the same or different, aryloxy or aryloxy substituted by one to three $R^{14}$, which may be the same or different, heteroaryloxy or heteroaryloxy substituted by one to three $R^{14}$, which may be the same or different, arylthio or arylthio substituted by one to three $R^{14}$, which may be the same or different, or heteroarylthio or heteroarylthio substituted by one to three $R^{14}$, which may be the same or different.

Most preferably $R^{10}$ is iso-propyl or tert-butyl.

Preferably each $R^{11}$ is independently $C_1$-$C_4$alkyl.

Preferably $R^{12}$ is $C_1$-$C_4$alkyl or $C_1$-$C_4$haloalkyl.

Preferably each $R^{13}$ is independently halo, nitro, $C_1$-$C_4$alkyl, $C_1$-$C_4$haloalkyl or $C_1$-$C_4$alkoxy. Examples of such preferred groups are chloro, fluoro, nitro, methyl, ethyl, trifluoromethyl and methoxy.

Preferably each $R^{14}$ is independently halo, nitro, $C_1$-$C_4$alkyl, $C_1$-$C_4$haloalkyl, $C_1$-$C_4$alkoxy or $C_1$-$C_4$haloalkoxy. Examples of such preferred groups are chloro, fluoro, nitro, methyl, ethyl, trifluoromethyl, methoxy and trifluoromethoxy.

In one embodiment the invention provides a method of controlling plants which comprises applying to the plants or to the locus thereof a herbicidally effective amount of a compound of formula (Ix)

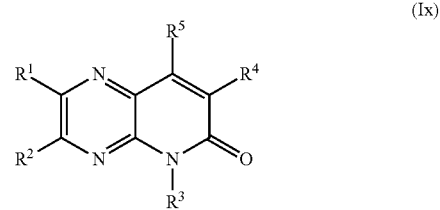

(Ix)

wherein $R^1$, $R^2$, $R^4$ and $R^5$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $R^1$, $R^2$, $R^4$, $R^5$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

In another embodiment the invention provides a method of controlling plants which comprises applying to the plants or to the locus thereof a herbicidally effective amount of a compound of formula (Ic)

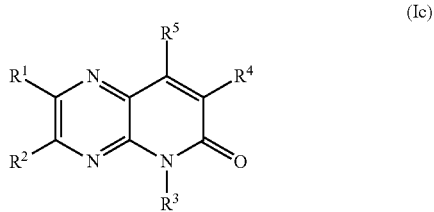

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is a group which can be metabolised to a hydroxy group; or a salt or N-oxide thereof. The preferences for $R^1$, $R^2$, $R^4$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen. The preferences for $R^5$ are the same as the preferences set out for the corresponding substituents of a compound of formula (I) except that $R^5$ cannot be hydroxy.

In another embodiment the invention provides a method of controlling plants which comprises applying to the plants or to the locus thereof a herbicidally effective amount of a compound of formula (Id)

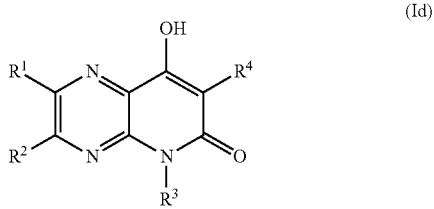

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $R^1$, $R^2$, $R^4$, $R^6$, $R^7$, $R^8$ and $R^{13}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

Certain compounds of formula (I) are novel and as such form a further aspect of the invention. One group of novel compounds are compounds of formula (Ib)

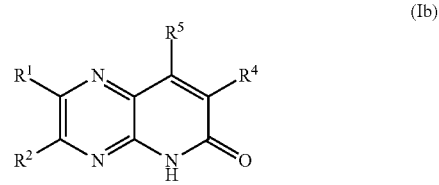

wherein $R^1$, $R^2$ and $R^4$ are as defined for compounds of formula (I) and $R^5$ is a group which can be metabolised to a hydroxy group; or a salt or N-oxide thereof. The preferences for $R^1$, $R^2$, $R^4$, $R^6$, $R^8$, $R^9$, $R^{10}$, $R^{11}$, $R^{12}$, $R^{13}$ and $R^{14}$ are the same as the preferences set out for the corresponding substituents of compounds of the formula (I). The preferences for $R^5$ are the same as the preferences set out for the corresponding substituents of compounds of formula (I) except that $R^5$ cannot be hydroxy.

Another group of novel compounds are compounds of formula (Ic)

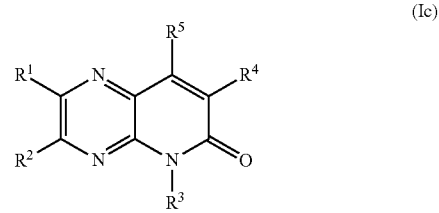

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is a group which can be metabolised to a hydroxy group; or a salt or N-oxide thereof. The preferences for $R^1$, $R^2$, $R^4$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen. The preferences for $R^5$ are the same as the preferences set out for the corresponding substituents of a compound of formula (I) except that $R^5$ cannot be hydroxy.

A further group of novel compounds are compounds of formula (Id)

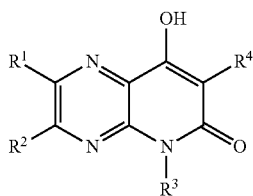

(Id)

wherein $R^1$, $R^2$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $R^1$, $R^2$, $R^4$, $R^6$, $R^7$, $R^8$ and $R^{13}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

The compounds in Tables 1 to 31 below illustrate the compounds of the invention.

TABLE 1

Table 1 provides 70 compounds of formula (I), where $R^1$ and $R^2$ are hydrogen, $R^4$ is 3,5-dichloro-pyrid-2-yl, and $R^3$ and $R^5$ have the values listed in Table 1.

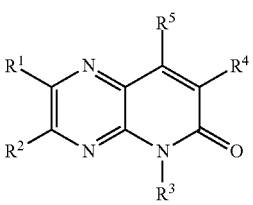

(I)

| Compound number | $R^3$ | $R^5$ |
|---|---|---|
| 1.001 | H | —OH |
| 1.002 | H | —OCOCH₃ |
| 1.003 | H | —OCOCH₂CH₃ |
| 1.004 | H | —OCOCH(CH₃)₂ |
| 1.005 | H | —OCO(CH₂)₂CH₃ |
| 1.006 | H | —OCOCH(CH₃)CH₂CH₃ |
| 1.007 | H | —OCOCH₂CH(CH₃)₂ |
| 1.008 | H | —OCOC(CH₃)₃ |
| 1.009 | H | —O(CO)OCH₂CH₃ |
| 1.010 | H | —O(CO)SCH₂CH₃ |
| 1.011 | —CH₃ | —OH |
| 1.012 | —CH₃ | —OCOCH₃ |
| 1.013 | —CH₃ | —OCOCH₂CH₃ |
| 1.014 | —CH₃ | —OCOCH(CH₃)₂ |
| 1.015 | —CH₃ | —OCO(CH₂)₂CH₃ |
| 1.016 | —CH₃ | —OCOCH(CH₃)CH₂CH₃ |
| 1.017 | —CH₃ | —OCOCH₂CH(CH₃)₂ |
| 1.018 | —CH₃ | —OCOC(CH₃)₃ |
| 1.019 | —CH₃ | —O(CO)OCH₂CH₃ |
| 1.020 | —CH₃ | —O(CO)SCH₂CH₃ |
| 1.021 | —CH₂CH₃ | —OH |
| 1.022 | —CH₂CH₃ | —OCOCH₃ |

TABLE 1-continued

Table 1 provides 70 compounds of formula (I), where $R^1$ and $R^2$ are hydrogen, $R^4$ is 3,5-dichloro-pyrid-2-yl, and $R^3$ and $R^5$ have the values listed in Table 1.

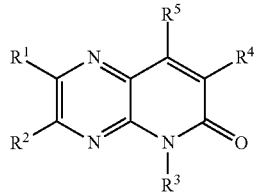

(I)

| Compound number | $R^3$ | $R^5$ |
|---|---|---|
| 1.023 | —CH₂CH₃ | —OCOCH₂CH₃ |
| 1.024 | —CH₂CH₃ | —OCOCH(CH₃)₂ |
| 1.025 | —CH₂CH₃ | —OCO(CH₂)₂CH₃ |
| 1.026 | —CH₂CH₃ | —OCOCH(CH₃)CH₂CH₃ |
| 1.027 | —CH₂CH₃ | —OCOCH₂ |
| 1.028 | —CH₂CH₃ | —OCOC(CH₃)₃ |
| 1.029 | —CH₂CH₃ | —O(CO)OCH(CH₃)₂ |
| 1.030 | —CH₂CH₃ | —O(CO)SCH₂CH₃ |
| 1.031 | —CH₂CHF₂ | —OH |
| 1.032 | —CH₂CHF₂ | —OCOCH₃ |
| 1.033 | —CH₂CHF₂ | —OCOCH₂CH₃ |
| 1.034 | —CH₂CHF₂ | —OCOCH(CH₃)₂ |
| 1.035 | —CH₂CHF₂ | —OCO(CH₂)₂CH₃ |
| 1.036 | —CH₂CHF₂ | —OCOCH(CH₃)CH₂CH₃ |
| 1.037 | —CH₂CHF₂ | —OCOCH₂CH(CH₃)₂ |
| 1.038 | —CH₂CHF₂ | —OCOC(CH₃)₃ |
| 1.039 | —CH₂CHF₂ | —O(CO)OCH₂CH₃ |
| 1.040 | —CH₂CHF₂ | —O(CO)SCH₂CH₃ |
| 1.041 | —CH₂CF₃ | —OH |
| 1.042 | —CH₂CF₃ | —OCOCH₃ |
| 1.043 | —CH₂CF₃ | —OCOCH₂CH₃ |
| 1.044 | —CH₂CF₃ | —OCOCH(CH₃)₂ |
| 1.045 | —CH₂CF₃ | —OCO(CH₂)₂CH₃ |
| 1.046 | —CH₂CF₃ | —OCOCH(CH₃)CH₂CH₃ |
| 1.047 | —CH₂CF₃ | —OCOCH₂CH(CH₃)₂ |
| 1.048 | —CH₂CF₃ | —OCOC(CH₃)₃ |
| 1.049 | —CH₂CF₃ | —O(CO)OCH₂CH₃ |
| 1.050 | —CH₂CF₃ | —O(CO)SCH₂CH₃ |
| 1.051 | —CH₂CH=CH₂ | —OH |
| 1.052 | —CH₂CH=CH₂ | —OCOCH₃ |
| 1.053 | —CH₂CH=CH₂ | —OCOCH₂CH₃ |
| 1.054 | —CH₂CH=CH₂ | —OCOCH(CH₃)₂ |
| 1.055 | —CH₂CH=CH₂ | —OCO(CH₂)₂CH₃ |
| 1.056 | —CH₂CH=CH₂ | —OCOCH(CH₃)CH₂CH₃ |
| 1.057 | —CH₂CH=CH₂ | —OCOCH₂CH(CH₃)₂ |
| 1.058 | —CH₂CH=CH₂ | —OCOC(CH₃)₃ |
| 1.059 | —CH₂CH=CH₂ | —O(CO)OCH₂CH₃ |
| 1.060 | —CH₂CH=CH₂ | —O(CO)SCH₂CH₃ |
| 1.061 | —CH₂C≡CH | —OH |
| 1.062 | —CH₂C≡CH | —OCOCH₃ |
| 1.063 | —CH₂C≡CH | —OCOCH₂CH₃ |
| 1.064 | —CH₂C≡CH | —OCOCH(CH₃)₂ |
| 1.065 | —CH₂C≡CH | —OCO(CH₂)₂CH₃ |
| 1.066 | —CH₂C≡CH | —OCOCH(CH₃)CH₂CH₃ |
| 1.067 | —CH₂C≡CH | —OCOCH₂CH(CH₃)₂ |
| 1.068 | —CH₂C≡CH | —OCOC(CH₃)₃ |
| 1.069 | —CH₂C≡CH | —O(CO)OCH₂CH₃ |
| 1.070 | —CH₂C≡CH | —O(CO)SCH₂CH₃ |

Table 2:

Table 2 provides 70 compounds of formula (I), where $R^1$ and $R^2$ are hydrogen, $R^4$ is 3,5-dichloro-pyrid-4-yl, and $R^3$ and $R^5$ have the values listed in Table 1.

Table 3:

Table 3 provides 70 compounds of formula (I), where $R^1$ and $R^2$ are hydrogen, $R^4$ is 2,6-dichloro-pyrid-3-yl, and $R^3$ and $R^5$ have the values listed in Table 1.

Table 4:
Table 4 provides 70 compounds of formula (I), where $R^1$ and $R^2$ are hydrogen, $R^4$ is 2,4-dichloro-pyrid-3-yl, and $R^3$ and $R^5$ have the values listed in Table 1.

Table 5:
Table 5 provides 70 compounds of formula (I), where $R^1$ and $R^2$ are hydrogen, $R^4$ is 4,6-dichloro-pyrid-3-yl, and $R^3$ and $R^5$ have the values listed in Table 1.

Table 6:
Table 6 provides 70 compounds of formula (I), where $R^1$ and $R^2$ are hydrogen, $R^4$ is 2,5-dichloro-pyrid-4-yl, and $R^3$ and $R^5$ have the values listed in Table 1.

Table 7:
Table 7 provides 70 compounds of formula (I), where $R^1$ and $R^2$ are hydrogen, $R^4$ is 3,6-dichloro-pyrid-2-yl, and $R^3$ and $R^5$ have the values listed in Table 1.

Table 8:
Table 8 provides 70 compounds of formula (I), where $R^1$ and $R^2$ are hydrogen, $R^4$ is 3-chloro-5-fluoro-pyrid-2-yl, and $R^3$ and $R^5$ have the values listed in Table 1.

Table 9:
Table 9 provides 70 compounds of formula (I), where $R^1$ and $R^2$ are hydrogen, $R^4$ is 3-chloro-5-trifluoromethyl-pyrid-2-yl, and $R^3$ and $R^5$ have the values listed in Table 1.

Table 10:
Table 10 provides 70 compounds of formula (I), where $R^1$ and $R^2$ are hydrogen, $R^4$ is 3,5,6-trichloro-pyrid-2-yl, and $R^3$ and $R^5$ have the values listed in Table 1.

Table 11:
Table 11 provides 70 compounds of formula (I), where $R^1$ and $R^2$ are hydrogen, $R^4$ is 2,5-dichloro-pyrid-3-yl, and $R^3$ and $R^5$ have the values listed in Table 1.

Table 12:
Table 12 provides 70 compounds of formula (I), where $R^1$ and $R^2$ are hydrogen, $R^4$ is 2,3-dichloro-pyrid-4-yl, and $R^3$ and $R^5$ have the values listed in Table 1.

Table 13:
Table 13 provides 70 compounds of formula (I), where $R^1$ and $R^2$ are hydrogen, $R^4$ is 2-chloro-4-trifluoromethyl-pyrid-3-yl, and $R^3$ and $R^5$ have the values listed in Table 1.

Table 14:
Table 14 provides 70 compounds of formula (I), where $R^1$ and $R^2$ are hydrogen, $R^4$ is 2-chloro-6-trifluoromethyl-pyrid-3-yl, and $R^3$ and $R^5$ have the values listed in Table 1.

Table 15:
Table 15 provides 70 compounds of formula (I), where $R^1$ and $R^2$ are hydrogen, $R^4$ is 3-chloro-5-trifluoromethyl-pyrid-4-yl, and $R^3$ and $R^5$ have the values listed in Table 1.

Table 16:
Table 16 provides 70 compounds of formula (I), where $R^1$ and $R^2$ are hydrogen, $R^4$ is 2,3,5-trichloro-pyrid-4-yl, and $R^3$ and $R^5$ have the values listed in Table 1.

Table 17
Table 17 provides 70 compounds of formula (I), where $R^1$ and $R^2$ are hydrogen, $R^4$ is 5-chloro-pyrimidin-4-yl, and $R^3$ and $R^5$ have the values listed in Table 1.

Table 18:
Table 18 provides 70 compounds of formula (I), where $R^1$ and $R^2$ are hydrogen, $R^4$ is 3,4,5-trichloro-thiophen-2-yl, and $R^3$ and $R^5$ have the values listed in Table 1.

Table 19:
Table 19 provides 70 compounds of formula (I), where $R^1$ and $R^2$ are hydrogen, $R^4$ is 2,5-dichloro-thiophen-3-yl, and $R^3$ and $R^5$ have the values listed in Table 1.

Table 20:
Table 20 provides 70 compounds of formula (I), where $R^1$ and $R^2$ are hydrogen, $R^4$ is 3-trifluoromethyl-isoxazol-5-yl, and $R^3$ and $R^5$ have the values listed in Table 1.

Table 21:
Table 21 provides 70 compounds of formula (I), where $R^1$ and $R^2$ are hydrogen, $R^4$ is 3-trifluoromethyl-4-chloro-isoxazol-5-yl, and $R^3$ and $R^5$ have the values listed in Table 1.

Table 22:
Table 22 provides 70 compounds of formula (I), where $R^1$ and $R^2$ are hydrogen, $R^4$ is 3,4-dichloro-isoxazol-5-yl, and $R^3$ and $R^5$ have the values listed in Table 1.

Table 23:
Table 23 provides 70 compounds of formula (I), where $R^1$ and $R^2$ are hydrogen, $R^4$ is 3-methyl-1,2,4-oxadiazol-5-yl, and $R^3$ and $R^5$ have the values listed in Table 1.

Table 24:
Table 24 provides 70 compounds of formula (I), where $R^1$ and $R^2$ are hydrogen, $R^4$ is 3-trifluoromethyl-1,2,4-oxadiazol-5-yl, and $R^3$ and $R^5$ have the values listed in Table 1.

Table 25:
Table 25 provides 70 compounds of formula (I), where $R^1$ and $R^2$ are hydrogen, $R^4$ is 2,4-dichloro-thiazol-5-yl, and $R^3$ and $R^5$ have the values listed in Table 1.

Table 26:
Table 26 provides 70 compounds of formula (I), where $R^1$ and $R^2$ are hydrogen, $R^4$ is 2-chloro-4-methyl-thiazol-5-yl, and $R^3$ and $R^5$ have the values listed in Table 1.

Table 27:
Table 27 provides 70 compounds of formula (I), where $R^1$ and $R^2$ are hydrogen, $R^4$ is 2,5-dichloro-thiazol-4-yl, and $R^3$ and $R^5$ have the values listed in Table 1.

Table 28:
Table 28 provides 70 compounds of formula (I), where $R^1$ and $R^2$ are hydrogen, $R^4$ is 2,4-dichloro-quinolin-3-yl, and $R^3$ and $R^5$ have the values listed in Table 1.

Table 29:
Table 29 provides 70 compounds of formula (I), where $R^1$ and $R^2$ are hydrogen, $R^4$ is 4-chloro-2-trifluoromethyl-quinolin-3-yl, and $R^3$ and $R^5$ have the values listed in Table 1.

Table 30:
Table 30 provides 70 compounds of formula (I), where $R^1$ and $R^2$ are hydrogen, $R^4$ is 1-chloro-isoquinolin-3-yl, and $R^3$ and $R^5$ have the values listed in Table 1.

Table 31
Table 31 provides 70 compounds of formula (I), where $R^1$ and $R^2$ are hydrogen, $R^4$ is 1,4-dichloro-isoquinolin-3-yl, and $R^3$ and $R^5$ have the values listed in Table 1.

The compounds of the invention may be made by a variety of methods, for example by the methods described in Schemes 1 to 10.

-continued

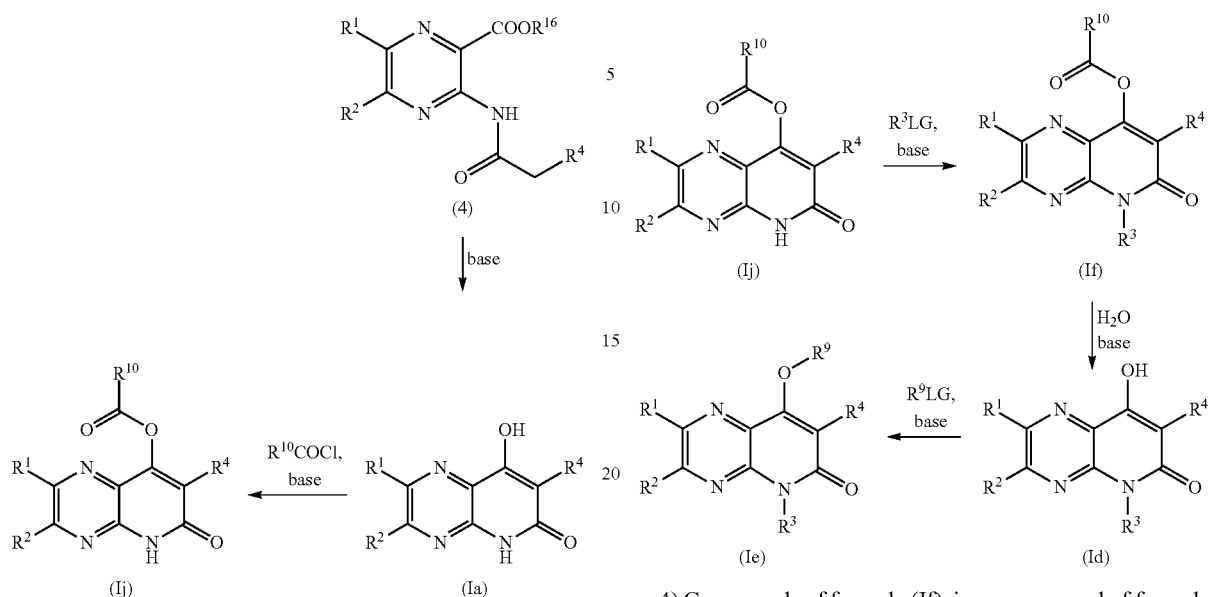

Scheme 2

1) Compounds of formula (4) wherein $R^1$, $R^2$ and $R^4$ are as defined for a compound of formula (I) and $R^{16}$ is $C_1$-$C_6$alkyl can be made by reaction of an amino-pyrazine ester of formula (2) wherein $R^1$ and $R^2$ are as defined for a compound of formula (I) and $R^{16}$ is $C_1$-$C_6$alkyl with an acid derivative of formula (3) wherein $R^4$ is as defined for a compound of formula (I) and X is halogen or hydroxy, as shown in Scheme 1. For example, if (3) is an acid chloride (i.e. where X is chlorine) the reaction can conveniently be carried out optionally in the presence of a base, such as triethylamine or pyridine, in a suitable solvent, such as acetonitrile or dichloromethane, optionally using microwave heating. Alternatively, if (3) is a carboxylic acid (i.e. where X is hydroxy) the reaction can conveniently be carried out using an amide coupling method, for example by reaction with a coupling agent, such as bis(2-oxo-3-oxazolidinyl)phosphinic chloride, in the presence of a base, such as triethylamine, in a suitable solvent, such as dichloromethane, or other amide coupling methods which have been reviewed in Tetrahedron (2005), 61(46), 10827-10852.

2) Compounds of formula (Ia) wherein $R^1$, $R^2$ and $R^4$ are as defined for a compound of formula (I) can be prepared by treating a compound of formula (4) as defined in 1) with a base in a suitable solvent, such as potassium carbonate in N,N-dimethylformamide or lithium hexamethyldisilazide in tetrahydrofuran, optionally using microwave heating.

3) Compounds of formula (Ij) wherein $R^1$, $R^3$, $R^4$ and $R^{10}$ are as defined for a compound of formula (I) can be prepared by reaction of a compound of formula (Ia) as defined in 2) with an acid chloride of formula $R^{10}COCl$ or an acid anhydride of formula $(R^{10}CO)_2O$ wherein $R^{10}$ is as defined for compounds of formula (I), optionally in the presence of a base, such as triethylamine or pyridine, optionally in a suitable solvent, such as dichloromethane.

4) Compounds of formula (If), i.e. a compound of formula (I) wherein $R^3$ is as defined for compound of formula (I) other than hydrogen and $R^5$ is —O—CO—$R^{10}$, can be prepared from a compound of formula (Ij) as defined in 3) by reaction with a compound of formula $R^3LG$ wherein $R^3$ is as defined for a compound of formula (I) and LG is a leaving group such as a halide, for example bromide or iodide, or tosylate, mesylate or triflate, in the presence of a base, such as potassium carbonate, optionally in the presence of an activator/iodide, such as potassium iodide, in a suitable solvent, such as acetonitrile or N,N-dimethylformamide, optionally using microwave heating, as shown in Scheme 2.

5) Compounds of formula (Id), i.e. a compound of formula (I) wherein $R^3$ is as defined for compounds of formula (I) other than hydrogen and $R^5$ is hydroxy, can be prepared by treating a compound of formula (If) as defined in 4) with a base, such as sodium hydroxide or potassium carbonate, and water in a suitable solvent, such as methanol or N,N-dimethylformamide.

6) Compounds of formula (Ie), i.e. compounds of formula (I) wherein $R^3$ is as defined for compound of formula (I) other than hydrogen and $R^5$ is —O—$R^9$, can be prepared from a compound of formula (Id) as defined in 5) by reaction with a compound of formula $R^9LG$ wherein $R^9$ is as defined for compounds of formula (I) and LG is a leaving group such halide, for example bromide or iodide, or tosylate, mesylate or triflate, in the presence of a base, such as potassium carbonate, in a suitable solvent, such as N,N-dimethylformamide.

Scheme 3

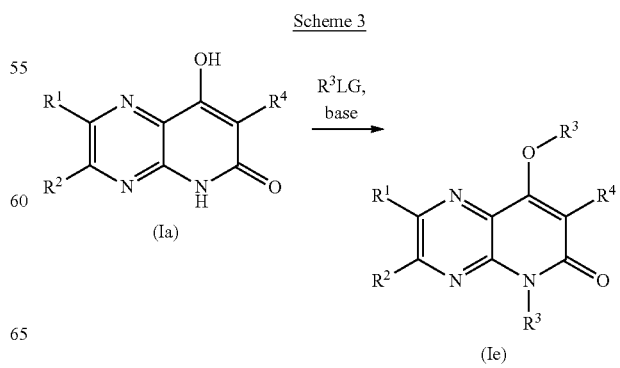

7) Where R³ and R⁹ happen to be identical, for example both are simple alkyl groups, compounds of formula (Ie) as defined in 6) can also be formed by reaction of a compound of formula (Ia) as defined in 2) with at least two equivalents of a compound of formula R³LG as defined in 4), in the presence of a base, such as potassium carbonate, in a suitable solvent, such as N,N-dimethylformamide, as shown in Scheme 3.

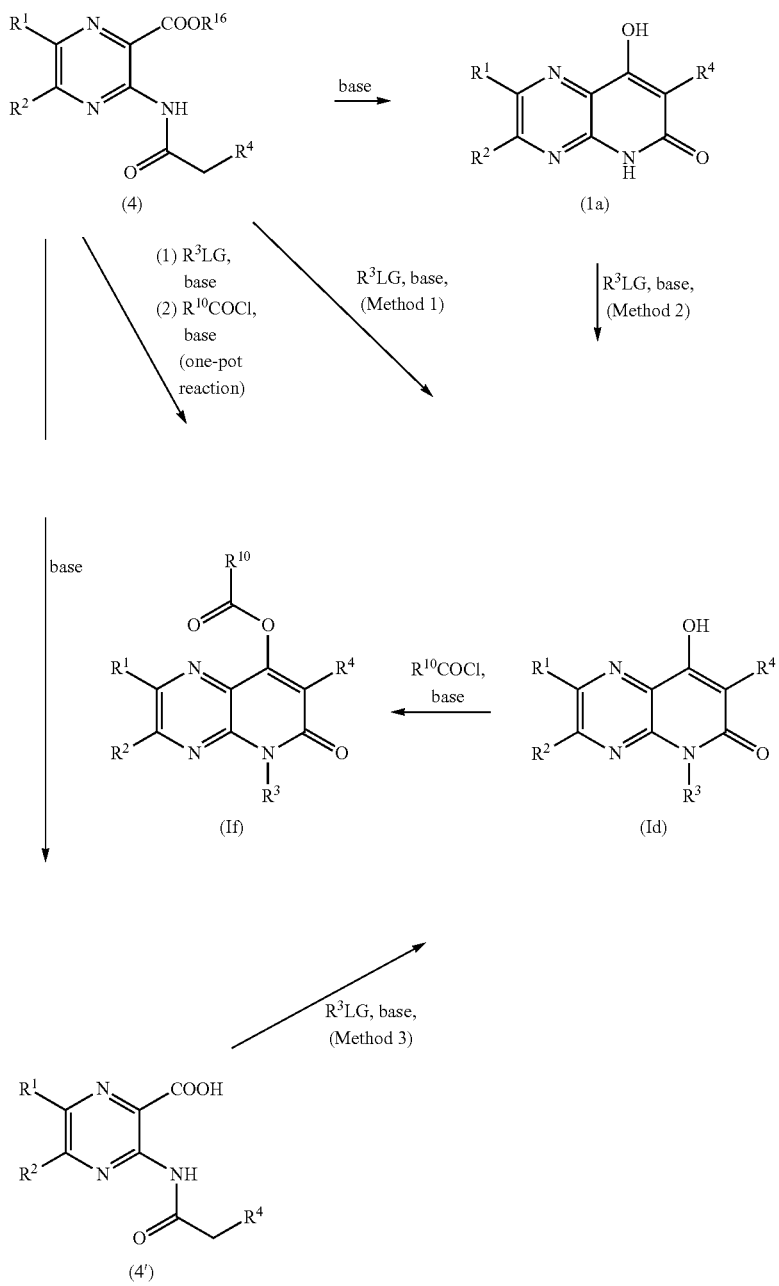

8) Compounds of formula (If) as defined in 4) can additionally be prepared in a shortened route directly from a compound of formula (4) as defined in 1) by reaction with a compound of formula $R^3LG$ as defined in 4), in the presence of a base, such as sodium or potassium hexamethyldisilazide, in a suitable solvent, such as tetrahydrofuran, optionally using microwave heating, followed by reaction with an acid chloride of formula $R^{10}COCl$ or an acid anhydride of formula $(R^{10}CO)_2O$ as defined in 3), optionally in the presence of a base, such as triethylamine, in the same reaction pot, as shown in Scheme 4.

9) Alternatively compounds of formula (If) as defined in 4) can be made from a compound of formula (Id) as defined in 5), by reaction with an acid chloride of formula $R^{10}COCl$ or an acid anhydride of formula $(R^{10}CO)_2O$ as defined in 3), optionally in the presence of a base, such as triethylamine, optionally in a suitable solvent, such as dichloromethane.

10) Compounds of formula (Id) as defined in 5) can be made by reaction of a compound of formula (4) as defined in 1) with a compound of formula $R^3LG$ as defined in 4), in the presence of a base, such as potassium hexamethyldisilazide, in a suitable solvent, such as tetrahydrofuran, optionally using microwave heating (Method 1).

11) Compounds of formula (Id) as defined in 5) can also be made from a compound of formula (Ia) as defined in 2) by reaction with a compound of formula $R^3LG$ as defined in 4), in the presence of a base, such as potassium hexamethyldisilazide, in a suitable solvent, such as tetrahydrofuran, optionally using microwave heating (Method 2). The synthesis of compounds of formula (Ia) was described under 2).

12) Compounds of formula (Ib) as defined in 5) can also be made by reaction of a compound of formula (4') with a compound of formula $R^3LG$ as defined in 4), in the presence of a base, such as sodium hexamethyldisilazide, in a suitable solvent, such as tetrahydrofuran, optionally using microwave heating (Method 3). Compounds of formula (4') can be made from a compound of formula (4) by reaction with a base, such as lithium hexamethyldisilazide, in a suitable solvent, such as tetrahydrofuran or N,N-dimethyl-formamide, optionally using microwave heating.

13) Silyl compounds of formula (Ig), i.e. a compound of formula (I) wherein $R^3$ is as defined for a compound of formula (I) other than hydrogen and $R^5$ is $-O-Si(R^{11})_3$, can be made from a compound of formula (Id) as defined in 5), by reaction with a trialkylsilyl chloride of formula $(R^{11})_3SiCl$, in a suitable solvent, such as tetrahydrofuran or acetonitrile, in the presence of a base, such as triethylamine, as shown in Scheme 5.

Scheme 6

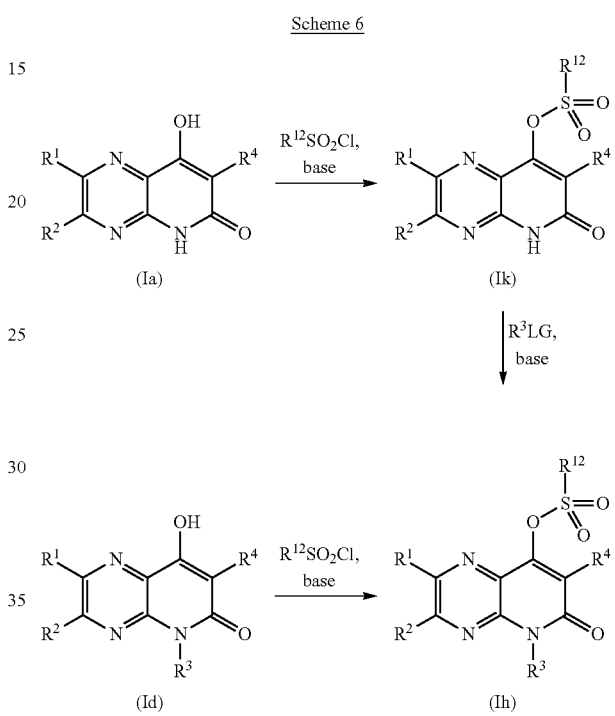

14) Sulfonyl compounds of formula (Ik) wherein $R^1$, $R^2$, $R^4$ and $R^{12}$ are as defined for a compound of formula (I) can be made from a compound of formula (Ia) as defined in 2) by reaction with a sulfonyl chloride of formula $R^{12}SO_2Cl$ wherein $R^{12}$ is as defined for a compound of formula (I), in the presence of a base, such as triethylamine, in a suitable solvent, such as tetrahydrofuran or dichloromethane, as shown in Scheme 6.

15) Sulfonyl compounds of formula (Ih), i.e. a compound of formula (I) wherein $R^3$ is as defined for compounds of formula (I) other than hydrogen and $R^5$ is $-O-SO_2-R^{12}$, can be made by reaction of a compound of formula (Ik) as defined in 13), with a compound of formula $R^3LG$ as defined in 4), in the presence of a base, such as sodium or potassium hexamethyldisilazide, in a suitable solvent, such as tetrahydrofuran, optionally using microwave heating.

16) Alternatively, compounds of formula (Ih) as defined in 14) can be made by reaction of a compound of formula (Id) as defined in 5) with a sulfonyl chloride of formula $R_{12}SO_2Cl$ as defined in 13), in the presence of a base, such as triethylamine, in a suitable solvent, such as tetrahydrofuran or dichloromethane.

Scheme 5

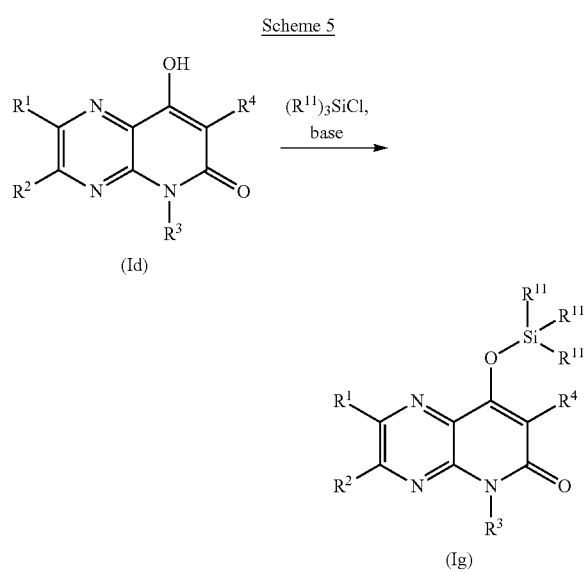

Scheme 7

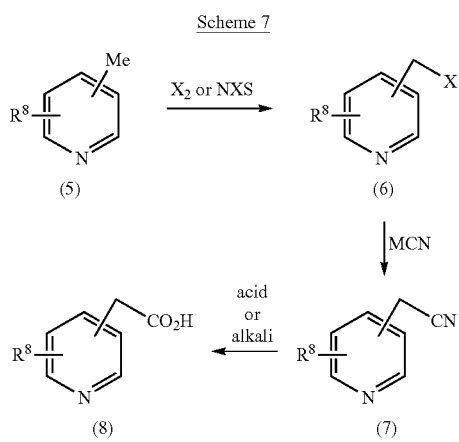

17) In certain cases where pyridyl acetic acids of formula (8) are not commercially available it is necessary to make them. A typical synthesis is shown in Scheme 7. Pyridylmethyl halides of formula (6) wherein $R^8$ is as defined for a compound of formula (I) and X is halogen, can be made by reaction of a substituted methyl-pyridine of formula (5) wherein $R^8$ is as defined for a compound of formula (I), with a halogenation agent, such as the halogen of formula $X_2$ wherein X is chlorine or bromine, in the presence of light, or a N-halosuccinimide of formula

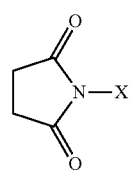

wherein X is chlorine, bromine or iodine, in the presence of a radical initiator, such as benzoyl peroxide, in a suitable solvent, such as carbon tetrachloride, and optionally in the presence of a light source, such as a 500 watt tungsten halogen lamp, at reflux.

18) Cyanomethyl-pyridines of formula (7) wherein $R^8$ is as defined for a compound of formula (I) can be made by reaction of a compound of formula (6) as defined in 17) with a metal cyanide, such as potassium cyanide, in a suitable solvent, such as ethanol, at reflux.

19) Pyridyl acetic acids of formula (8) wherein $R^8$ is as defined for a compound of formula (I) can be made by reaction of a compound of formula (7) as defined in 18) by hydrolysis using aqueous acid or alkali, but preferably aqueous acid, such as aqueous sulfuric acid, at reflux.

Scheme 8

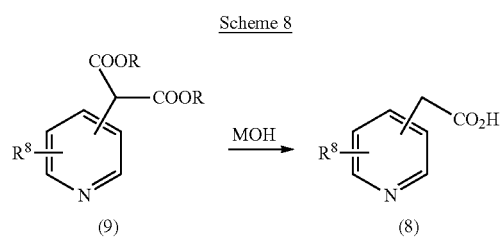

20) Pyridyl acetic acids of formula (8) can be made by hydrolysis of pyridyl malonates of formula (9), in the presence of, for example, an alkali metal hydroxide MOH, where M is sodium or potassium, in the a suitable solvent, such as methanol or ethanol, optionally in the presence of water.

Scheme 9

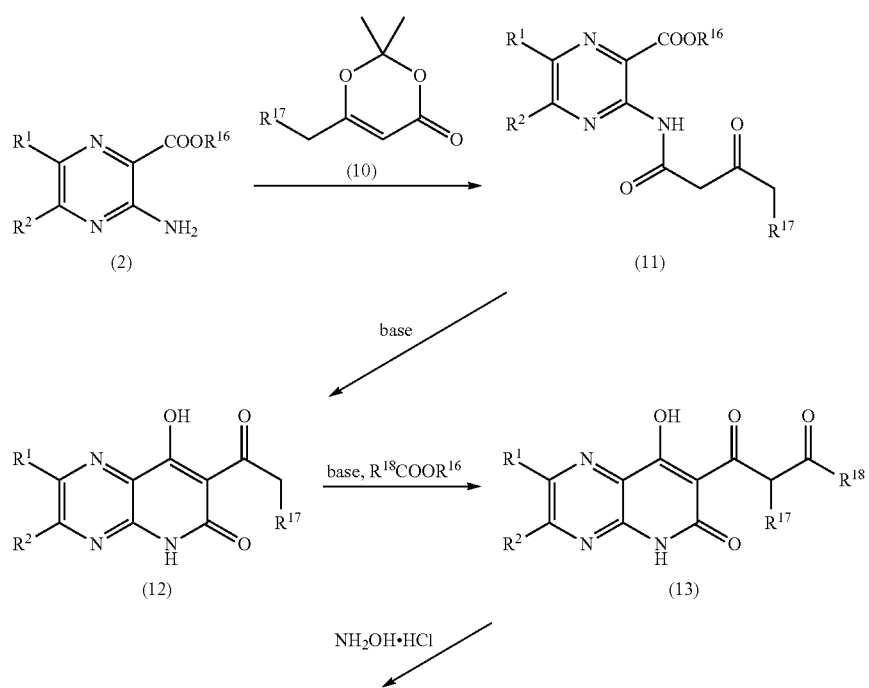

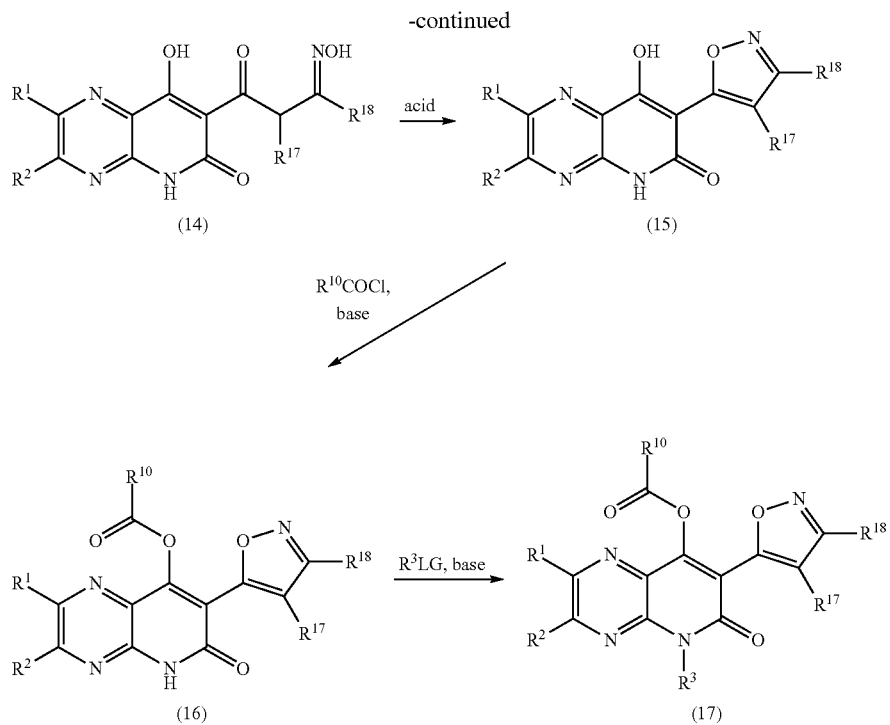

21) Diketo amides of formula (11), wherein $R^1$ and $R^2$ are as defined for a compound of formula (I), $R^{16}$ is as defined in 1) and $R^{17}$ is hydrogen, $C_1$-$C_6$ alkyl, $C_1$-$C_4$haloalkyl, aryl or aryl substituted by one to five $R^8$, which may be the same or different, or heteroaryl or heteroaryl substituted by one to four $R^8$, which may be the same or different, can be made by reacting a compound of formula (2) as defined in 1) with a compound of formula (10), wherein $R^{17}$ is hydrogen, $C_1$-$C_6$ alkyl, $C_1$-$C_4$haloalkyl, aryl or aryl substituted by one to five $R^8$, which may be the same or different, or heteroaryl or heteroaryl substituted by one to four $R^8$, which may be the same or different, in a suitable solvent, such as toluene, at a temperature range from 75° C. to 150° C., preferably at reflux, as shown in Scheme 9.

22) Compounds of formula (12), wherein $R^1$ and $R^2$ are as defined for a compound of formula (I), and $R^{17}$ is as defined in 21), can be made from a compound of formula (11) as defined in 21), by heating with a suitable base, such as an alkali metal alkoxide, for example sodium methoxide, in a suitable solvent, such as methanol, preferably at reflux.

23) Compounds of formula (13), wherein $R^1$ and $R^2$ are as defined for a compound of formula (I), $R^{17}$ is as defined in 21), and $R^{18}$ is $C_1$-$C_6$ alkyl, $C_1$-$C_4$haloalkyl, aryl or aryl substituted by one to five $R^8$, which may be the same or different, or heteroaryl or heteroaryl substituted by one to four $R^8$, which may be the same or different, can be made from a compound of formula (12) as defined in 22) by reaction with an ester of formula $R^{18}COOR^{16}$, wherein $R^{18}$ is $C_1$-$C_6$ alkyl, $C_1$-$C_4$haloalkyl, aryl or aryl substituted by one to five $R^8$, which may be the same or different, or heteroaryl or heteroaryl substituted by one to four $R^8$, which may be the same or different, and $R^{16}$ is as defined in 1), with a suitable base, such as sodium or sodium hydride, in $R^{18}COOR^{16}$ as solvent, or alternatively with a co-solvent, such as toluene, at a temperature range from 40° C. to 100° C., preferably from 50° C. to 75° C.

24) Compounds of formula (14), wherein $R^1$ and $R^2$ are as defined for a compound of formula (I), $R^{17}$ is defined as in 21), and $R^{18}$ is defined as in 23), can be made from a compound of formula (13) as defined in 23) by heating with hydroxylamine or its salts, in a suitable solvent, such as ethanol, preferably at reflux.

(25) Compounds of formula (15), wherein $R^1$ and $R^2$ are as defined for a compound of formula (I), $R^{17}$ is defined as in 21), and $R^{18}$ is defined as in 23), can be made from a compound of formula (14) as defined in 24) by heating with a suitable acid, such as acetic acid or trifluoroacetic acid, preferably at reflux.

(26) Compounds of formula (16), wherein $R^1$, $R^2$ and $R^{10}$ are as defined for a compound of formula (I), $R^{17}$ is defined as in 21), and $R^{18}$ is defined as in 23), can be made by reacting a compound of formula (15) as defined in 25) with an acid chloride of formula $R^{10}COCl$ as defined in 3) in the presence of base, such as pyridine, in a suitable solvent, such as dichloromethane, preferably at ambient temperature.

(27) Compounds of formula (17), wherein $R^1$, $R^2$ and $R^{10}$ are as defined for a compound of formula (I), $R^3$ is as defined for a compound of formula (I) other than hydrogen hydrogen, $R^{17}$ is defined as in 21), and $R^{18}$ is defined as in 23), can be made by reacting a compound of formula (16) as defined in 26) with a compound of formula $R^3LG$ as defined in 4), and suitable base, such as potassium carbonate, in a suitable solvent, such as N,N-dimethylformamide, with heating, optionally in a microwave, at a temperature range from 50° C. to 150° C., preferably from 80° C. to 120° C.

Scheme 10

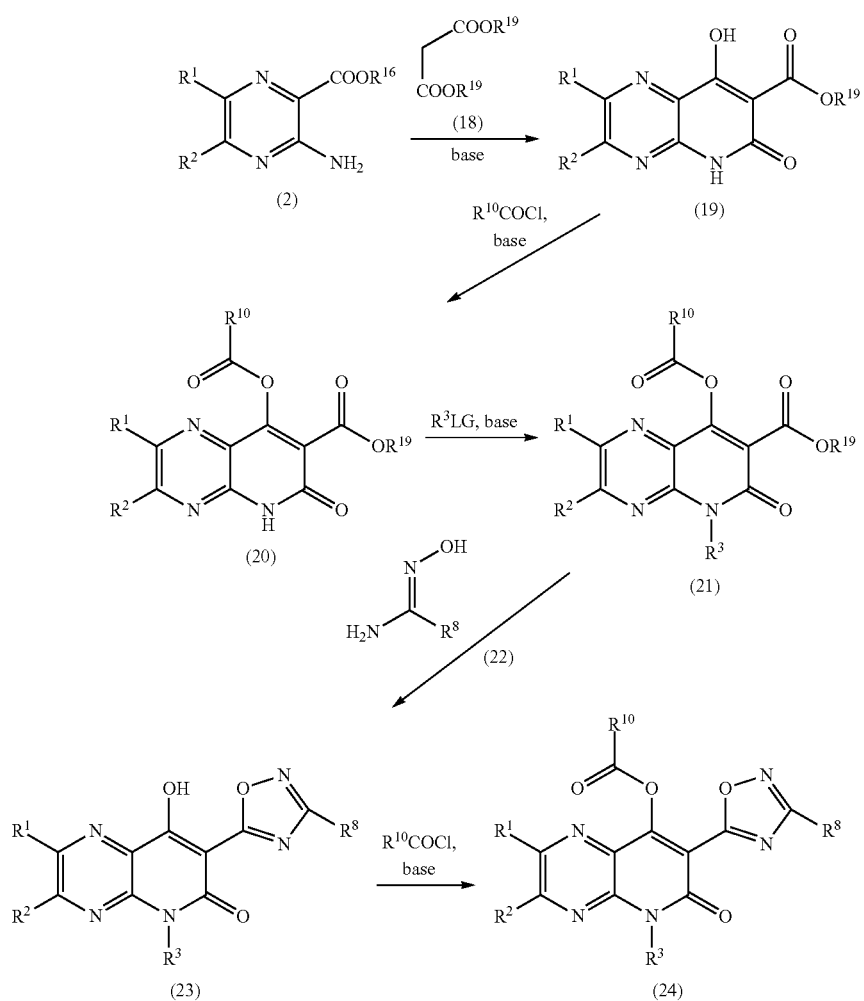

28) Compounds of formula (19), wherein $R^1$ and $R^2$ are as defined for a compound of formula (I) and $R^{19}$ is $C_1$-$C_6$alkyl, can be made by reaction of an aminopyrazine ester of formula (2) as defined under 1) with a dialkyl malonate of formula $CH_2(CO_2R^{19})_2$ wherein $R^{19}$ is $C_1$-$C_6$alkyl, in the presence of a base, such as sodium methoxide, in a suitable solvent, such as methanol, at a temperature range from 25° C. to 80° C., preferably from 40° C. to 65° C., as shown in Scheme 10.

29) Compounds of formula (20), wherein $R^1$, $R^2$ and $R^{10}$ are as defined for a compound of formula (I) and $R^{19}$ is $C_1$-$C_6$alkyl, can be made by reaction of a compound of formula (19) as defined in 28) with an acid chloride of formula $R^{10}COCl$ as defined in 3), in the presence of base, such as pyridine, in a suitable solvent, such as 1,2-dichloroethane, at a temperature range from 25° C. to 100° C., preferably from 60° C. to 85° C.

30) Compounds of formula (21), wherein $R^1$, $R^2$ and $R^{10}$ are as defined for a compound of formula (I), $R^3$ is as defined for a compound of formula (I) other than hydrogen, and $R^{19}$ is $C_1$-$C_6$alkyl, can be made from a compound of formula (20) as defined in 29) by reaction with a compound of formula $R^3LG$ as defined in 4), in the presence of a suitable base, such as potassium carbonate, in a suitable solvent, such as N,N-dimethylformamide, at a temperature range from 50° C. to 150° C., preferably from 80° C. to 120° C., optionally in a microwave.

31) Compounds of formula (23), wherein $R^1$, $R^2$ and $R^8$ are as defined for a compound of formula (I), and $R^3$ is as defined for a compound of formula (I) other than hydrogen, can be made from a compound of formula (21) as defined in 30) by heating with a hydroxy-amidine of formula (22), wherein $R^8$ is as defined for a compound of formula (I), in a suitable solvent, such as toluene, preferably at reflux.

32) Compounds of formula (24), wherein $R^1$, $R^2$, $R^8$ and $R^{10}$ are as defined for a compound of formula (I), and $R^3$ is as defined for a compound of formula (I) other than hydrogen, can be made by reacting a compound of formula (23) with an acid chloride of formula $R^{10}COCl$ as defined in 3), in the presence of a base, such as pyridine, in a suitable solvent, such as dichloromethane.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octa-decanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. CaCO$_3$ or SiO$_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention relates to a method of controlling plants which comprises applying to the plants or to the locus thereof a herbicidally effective amount of a compound of formula (I).

The invention also relates to a method of inhibiting plant growth which comprises applying to the plants or to the locus thereof a herbicidally effective amount of a compound of formula (I).

The invention also relates to a method of selectively controlling grasses and weeds in crops of useful plants which comprises applying to the useful plants or locus thereof or to the area of cultivation a herbicidally effective amount of a compound of formula (I).

Crops of useful plants in which the composition according to the invention can be used include perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals and vegetables, especially cereals and maize.

The grasses and weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

Areas under cultivation include land on which the crop plants are already growing and land intended for cultivation with those crop plants.

The compounds of formula (I) according to the invention can also be used in combination with one or more further herbicides. In particular, the following mixtures of the compound of formula (I) are important:

Mixtures of a compound of formula (I) with a synthetic auxin (e.g. compound of formula (I)+clopyralid (162), compound of formula (I)+2,4-D (211), compound of formula (I)+dicamba (228), compound of formula (I)+MCPA (499), compound of formula (I)+quinclorac (712), or compound of formula (I)+aminopyralid (CAS RN 150114-71-9)).

Mixtures of a compound of formula (I) with diflufenzopyr (252).

Mixtures of a compound of formula (I) with an acetanilide (e.g. compound of formula (I)+acetochlor (5), compound of formula (I)+dimethenamid (260), compound of formula (I)+metolachlor (548), compound of formula (I)+S-metolachlor (549), compound of formula (I)+pretilachlor (656)).

Mixtures of a compound of formula (I) with flamprop-M (355).

Mixtures of a compound of formula (I) with flufenacet (BAY FOE 5043) (369).

Mixtures of a compound of formula (I) with pyroxasulfone (CAS RN 447399-55-5).

Mixtures of a compound of formula (I) with a triazine (e.g. compound of formula (I)+atrazine (37), or compound of formula (I)+terbuthylazine (775)).

Mixtures of a compound of formula (I) with an HPPD inhibitor (e.g. compound of formula (I)+isoxaflutole (479), compound of formula (I)+mesotrione (515), compound of formula (I)+pyrasulfotole (CAS RN 365400-11-9), compound of formula (I)+sulcotrione (747), compound of formula (I)+tembotrione (CAS RN 335104-84-2), compound of formula (I)+topramezone (CAS RN 210631-68-8), compound of formula (I)+4-hydroxy-3-[[2-[(2-methoxyethoxy)methyl]-6-(trifluoromethyl)-3-pyridinyl]carbonyl]-bicyclo [3.2.1]oct-3-en-2-one (CAS RN 352010-68-5), or compound of formula (I)+4-hydroxy-3-[[2-(3-methoxypropyl)-6-(difluoromethyl)-3-pyridinyl]carbonyl]-bicyclo[3.2.1]oct-3-en-2-one (CAS RN 894355-80-7)).

Mixtures of a compound of formula (I) with an HPPD inhibitor and a triazine.

Mixtures of a compound of formula (I) with glyphosate (419).

Mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+glyphosate+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glufosinate-ammonium (418).

Mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+glufosinate-ammonium+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with an ALS or an AHAS inhibitor (e.g. compound of formula (I)+bensulfuron-methyl (64), compound of formula (I)+chlorimuron-ethyl (135), compound of formula (I)+cloransulam-methyl (164), compound of formula (I)+florasulam (359), compound of formula (I)+flucarbazone-sodium (364), compound of formula (I)+imazamox (451), compound of formula (I)+imazapyr (453), compound of formula (I)+imazethapyr (455), compound of formula (I)+iodosulfuron-methyl-sodium (466), compound of formula (I)+mesosulfuron-methyl (514), compound of formula (I)+nicosulfuron (577), compound of formula (I)+penoxsulam (622), compound of formula (I)+pyroxsulam (triflosulam) (CAS RN 422556-08-9), compound of formula (I)+thifensulfuron-methyl (thiameturon-methyl) (795), compound of formula (I)+triasulfuron (817), compound of formula (I)+tribenuron-methyl (822), compound of formula (I)+trifloxysulfuron-sodium (833), compound of formula (I)+thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or compound of formula (I)+thiencarbazone-methyl (methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula (I) with a PPO inhibitor (e.g. compound of formula (I)+butafenacil (101), compound of formula (I)+carfentrazone-ethyl (121), compound of formula (I)+cinidon-ethyl (152), compound of formula (I)+flumioxazin (376), compound of formula (I)+fomesafen (401), or compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6).

Mixtures of a compound of formula (I) with an ACCase inhibitor (e.g. compound of formula (I)+butroxydim (106), compound of formula (I)+clethodim (155), compound of formula (I)+clodinafop-propargyl (156), compound of formula (I)+cycloxydim (190), compound of formula (I)+cyhalofop-butyl (195), compound of formula (I)+diclofop-methyl (238), compound of formula (I)+fenoxaprop-P-ethyl (339), compound of formula (I)+fluazifop-butyl (361), compound of formula (I)+fluazifop-P-butyl (362), compound of formula (I)+haloxyfop (427), compound of formula (I)+haloxyfop-P (428), compound of formula (I)+propaquizafop (670), compound of formula (I)+quizalofop (717), compound of formula (I)+quizalofop-P (718), compound of formula (I)+sethoxydim (726), compound of formula (I)+tepraloxydim (771), compound of formula (I)+tralkoxydim (811)), or compound of formula (I)+pinoxaden (CAS RN 243973-20-8).

Mixtures of a compound of formula (I) with prosulfocarb (683), or a compound of formula (I) with tri-allate (816).

Mixtures of a compound of formula (I) with bromoxynil (95), a compound of formula (I) with chloridazon (134), a compound of formula (I) with chlorotoluron (143), a compound of formula (I) with diuron (281), or a compound of formula (I) with metribuzin (554).

Mixtures of a compound of formula (I) with clomazone (159), a compound of formula (I) with diflufenican (251), a compound of formula (I) with fluorochloridone (389), or a compound of formula (I) with flurtamone (392).

Mixtures of a compound of formula (I) with pendimethalin (621) or a compound of formula (I) with trifluralin (836).

Mixtures of a compound of formula (I) with difenzoquat metilsulfate (248).

Mixtures of a compound of formula (I) with diquat dibromide (276).

Mixtures of a compound of formula (I) with paraquat dichloride (614).

The mixing partners of the compound of formula (I) may also be in the form of esters or salts, as mentioned e.g. in The Pesticide Manual, 13$^{th}$ Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

Additionally, one or more of the following herbicides can be used in combination with a compound of formula (I) according to the invention or in combination with a mixture as described above: acifluorfen-sodium (7), aclonifen (8), acrolein (10), alachlor (14), alloxydim (18), ametryn (20), amicarbazone (21), amidosulfuron (22), amitrole (aminotriazole) (25), ammonium sulfamate (26), anilofos (31), asulam (36), aviglycine (39), azafenidin (CAS RN 68049-83-2), azimsulfuron (43), BAS 800H (CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorflurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), caimuron (213), dalapon (214), dazomet (216), desmedipham (225), desmetryn (CAS RN 1014-69-3), dichlobenil (229), dichlorprop (234), dichlorprop-P (235), diclosulam (241), dimefuron (256), dimepiperate (257), dimethachlor (258), dimethametryn (259), dimethipin (261), dimethylarsinic acid (264), dinitramine (268), dinoterb (272), diphenamid (274), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuron-methyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), fluometuron (378), fluoroglycofen-ethyl (380), flupoxam (CAS RN 119126-15-7), flupropacil (CAS RN 120890-70-2), flupropanate (383), flupyrsulfuron-methyl-sodium (384), flurenol (387), fluridone (388), fluoroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lactofen (486), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), naproanilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (propcarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluoron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3) and tritosulfuron (843).

The mixing partners of the compound of formula (I) may also be in the form of esters or salts, as mentioned e.g. in The Pesticide Manual, 13th Edition (BCPC), 2003. The reference to acifluorfen-sodium also applies to acifluorfen, and the reference to bensulfuron-methyl also applies to bensulfuron, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further herbicides can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. The safeners can be benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) and the corresponding R isomer, isoxadifen-ethyl (478), mefen-pyr-diethyl (506), naphthalic anhydride (CAS RN 81-84-5), and oxabetrinil (598). Particularly preferred are mixtures of a compound of formula (I) with benoxacor and a compound of formula (I) with cloquintocet-mexyl.

The safeners of the compound of formula (I) may also be in the form of esters or salts, as mentioned e.g. in The Pesticide Manual, 13th Edition (BCPC), 2003. The reference to cloquintocet-mexyl also applies to cloquintocet, and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) with the safener). It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with a triazine and a safener.
Mixtures of a compound of formula (I) with glyphosate and a safener.
Mixtures of a compound of formula (I) with glufosinate and a safener.
Mixtures of a compound of formula (I) with S-metolachlor and a safener, particularly benoxacor.
Mixtures of a compound of formula (I) with isoxaflutole and a safener.
Mixtures of a compound of formula (I) with isoxaflutole and a triazine and a safener.
Mixtures of a compound of formula (I) with isoxaflutole and glyphosate and a safener.
Mixtures of a compound of formula (I) with isoxaflutole and glufosinate and a safener.
Mixtures of a compound of formula (I) with mesotrione and a safener.
Mixtures of a compound of formula (I) with mesotrione and a triazine and a safener.
Mixtures of a compound of formula (I) with mesotrione and glyphosate and a safener.
Mixtures of a compound of formula (I) with mesotrione and glufosinate and a safener.
Mixtures of a compound of formula (I) with sulcotrione and a safener.
Mixtures of a compound of formula (I) with sulcotrione and a triazine and a safener.
Mixtures of a compound of formula (I) with sulcotrione and glyphosate and a safener.
Mixtures of a compound of formula (I) with sulcotrione and glufosinate and a safener.
Mixtures of a compound of formula (I) with clodinafop-propargyl and a safener, particularly cloquintocet-mexyl.

The following Examples further illustrate, but do not limit, the invention.

PREPARATION EXAMPLES

1. Reactions which are Covered by Schemes 1 and 2 where $R^4$ is a 6-Membered Ring Example 1.1

Preparation of 3-[2-(3,5-dichloro-pyrid-2-yl)-acetylamino]-pyrazine-2-carboxylic acid methyl ester

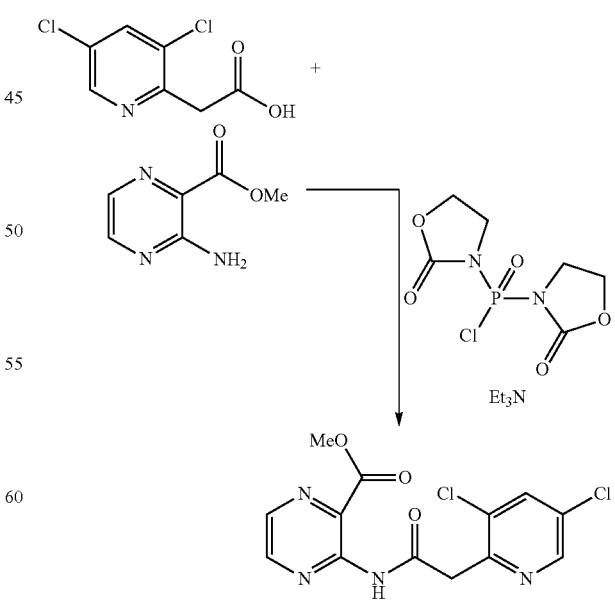

To a solution of (3,5-dichloro-pyrid-2-yl)-acetic acid (Example 5.1) (5.7 g) and 3-amino-pyrazine-2-carboxylic acid methyl ester (4.65 g) in dichloromethane (120 ml) were added successively triethylamine (8.5 ml) and bis(2-oxo-3-oxazolidinyl)phosphinic chloride (7.5 g). The reaction mixture was stirred at ambient temperature for 24 hours. The organic phase was washed successively with water, aqueous sodium hydrogen carbonate (1M), and brine. The organic phase was dried over magnesium sulfate and concentrated to give 3-[2-(3,5-dichloro-pyrid-2-yl)-acetylamino]-pyrazine-2-carboxylic acid methyl ester (6.37 g). $^1$H-NMR (400 MHz, CDCl$_3$): 4.04 (s, 3H), 4.35 (s, 2H), 7.77 (s, 1H), 8.39 (s, 1H), 8.49 (s, 1H), 8.56 (s, 1H), 11.02 (s, 1H) ppm.

Example 1.2

Preparation of 7-(3,5-dichloro-pyrid-2-yl)-pyrido[2,3-b]pyrazine-6,8-diol (Compound No. A1 of Table A)

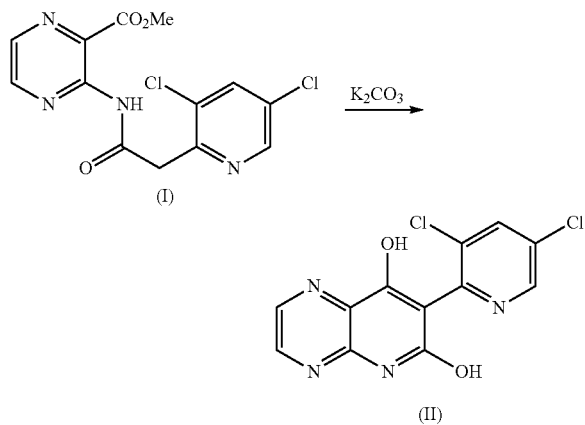

A mixture of 3-[2-(3,5-dichloro-pyrid-2-yl)-acetylamino]-pyrazine-2-carboxylic acid methyl ester (Example 1.1) (5.78 g) and potassium carbonate (2.4 g) in dry N,N-dimethylformamide (100 ml) was heated to 100° C. for 2 hours. The reaction mixture was cooled to ambient temperature and concentrated. The residue was triturated with diethyl ether and the organic phase decanted. The solid was dissolved in water and pH value adjusted to pH 5 by addition of aqueous hydrochloric acid (2M). The aqueous phase was concentrated. The residue was dissolved in methanol, the insoluble salts were removed by filtration and the filtrate was concentrated to give Compound No. A1 of Table A (4.9 g).

Example 1.3

Preparation of isobutyric acid 7-(3,5-dichloro-pyrid-2-yl)-6-oxo-5,6-dihydro-pyrido[2,3-b]pyrazin-8-yl ester (Compound No. A5 of Table A)

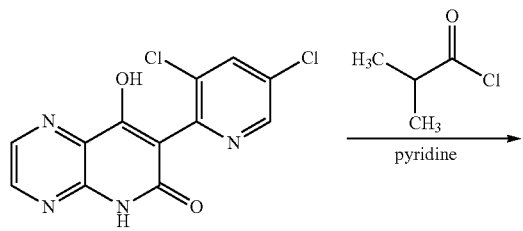

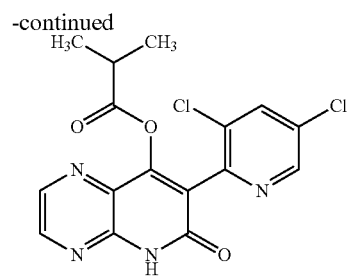

7-(3,5-Dichloro-pyrid-2-yl)-pyrido[2,3-b]pyrazine-6,8-diol (Example 1.2) (1.6 g) was dissolved in dichloromethane (50 ml) containing pyridine (0.445 g) and the reaction mixture stirred for 10 minutes. Isobutyryl chloride (0.556 g) was added dropwise over 5 minutes and the reaction mixture stirred for two hours. Water was added and the mixture extracted with ethyl acetate. The phases were separated and the organic fraction was washed with aqueous sodium carbonate (1M). The organic fraction was dried over sodium sulfate and concentrated to give a pale yellow solid which was recrystallized from ethyl acetate/hexane to give Compound No. A5 of Table A (1.02 g).

The following compound was made by an analogous method:

Carbonic acid 7-(3,5-dichloro-pyrid-2-yl)-6-oxo-5,6-dihydro-pyrido[2,3-b]pyrazin-8-yl ester ethyl ester (Compound No. A3 of Table A) from 7-(3,5-dichloro-pyrid-2-yl)-pyrido[2,3-b]pyrazine-6,8-diol (Example 1.2) using ethyl chloroformate as reagent.

Example 1.4

Preparation of isobutyric acid 7-(3,5-dichloro-pyrid-2-yl)-5-ethyl-6-oxo-5,6-dihydro-pyrido[2,3-b]pyrazin-8-yl ester (Compound No. A6 of Table A)

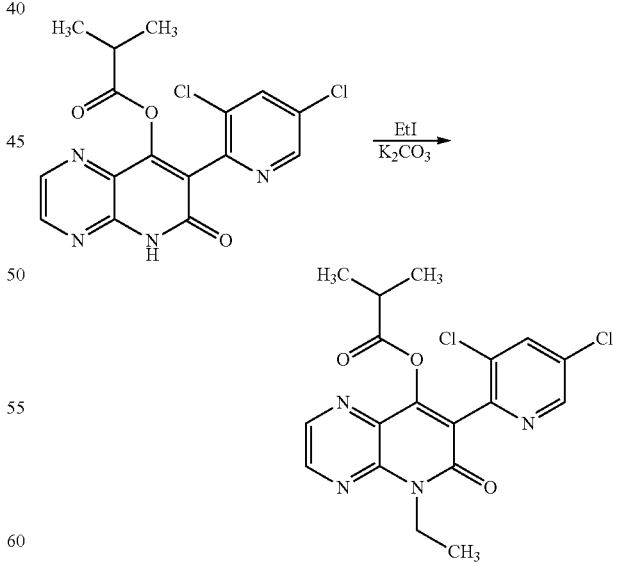

Isobutyric acid 7-(3,5-dichloro-pyrid-2-yl)-6-oxo-5,6-dihydro-pyrido[2,3-b]pyrazin-8-yl ester (Example 1.3) (0.250 g) was dissolved in acetonitrile (2 ml) and potassium carbonate (0.138 g) and ethyl iodide (0.1 ml) were added successively. The reaction mixture was heated in a microwave at 100° C. for 11 minutes, cooled to ambient temperature and concentrated. The residue was purified by column chromatography on silica gel (eluent: hexane/ethyl acetate 1:1) to give Compound No. A6 of Table A as a yellow gum which solidified on standing (0.101 g).

The following compounds were made by analogous methods:

Isobutyric acid 7-(3,5-dichloro-pyrid-2-yl)-5-methyl-6-oxo-5,6-dihydro-pyrido[2,3-b]pyrazin-8-yl ester (Compound No. A7 of Table A) from isobutyric acid 7-(3,5-dichloro-pyrid-2-yl)-6-oxo-5,6-dihydro-pyrido[2,3-b] pyrazin-8-yl ester (Example 1.3) using methyl iodide as reagent.

Carbonic acid 7-(3,5-dichloro-pyrid-2-yl)-5-methyl-6-oxo-5,6-dihydro-pyrido-[2,3-b]pyrazin-8-yl ester ethyl ester (Compound No. A2 of Table A) from carbonic acid 7-(3,5-dichloro-pyrid-2-yl)-6-oxo-5,6-dihydro-pyrido[2,3-b] pyrazin-8-yl ester ethyl ester (Example 1.3) using methyl iodide as reagent.

2,2-Dimethyl-propionic acid 7-(3,5-dichloro-pyrid-4-yl)-5-methyl-6-oxo-5,6-dihydro-pyrido[2,3-b]pyrazin-8-yl ester (Compound No. A9 of Table A) from 2,2-dimethyl-propionic acid 7-(3,5-dichloro-pyrid-4-yl)-6-oxo-5,6-dihydro-pyrido[2,3-b]pyrazin-8-yl ester (Example 1.7) using methyl iodide as reagent.

2,2-Dimethyl-propionic acid 7-(3,5-dichloro-pyrid-4-yl)-5-ethyl-6-oxo-5,6-dihydro-pyrido[2,3-b]pyrazin-8-yl ester (Compound No. A10 of Table A) from 2,2-dimethyl-propionic acid 7-(3,5-dichloro-pyrid-4-yl)-6-oxo-5,6-dihydro-pyrido[2,3-b]pyrazin-8-yl ester (Example 1.7) using ethyl iodide as reagent.

2,2-Dimethyl-propionic acid 7-(2,6-dichloro-pyrid-3-yl)-5-methyl-6-oxo-5,6-dihydro-pyrido[2,3-b]pyrazin-8-yl ester (Compound No. A15 of Table A) from 2,2-dimethyl-propionic acid 7-(2,6-dichloro-pyrid-3-yl)-6-oxo-5,6-dihydro-pyrido[2,3-b]pyrazin-8-yl ester (Example 1.7) using methyl iodide as reagent.

Example 1.5

Preparation of 3-[2-(2,6-dichloro-pyrid-3-yl)-acetylamino]-pyrazine-2-carboxylic acid methyl ester

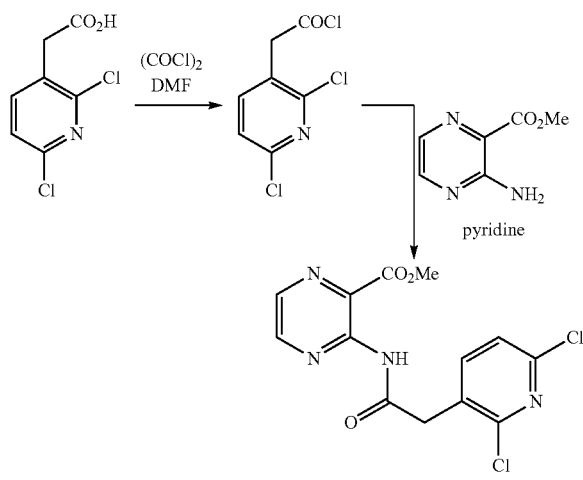

(2,6-Dichloro-pyrid-3-yl)-acetyl chloride was formed by dropwise addition of oxalyl chloride to a solution of (2,6-dichloro-pyrid-3-yl)-acetic acid (Example 4.3) (1.174 g) in dichloromethane (10 ml) with two drops of N,N-dimethylformamide. The reaction mixture was stirred at ambient temperature for 2 hours. The reaction mixture was then concentrated to give the acid chloride as an oil, which used without purification in the next step. To a suspension of methyl 3-amino-pyrazine 2-carboxylate (0.870 g) in dichloromethane (20 ml) and pyridine (0.463 ml) was added dropwise a solution of the acid chloride in dichloromethane (10 ml). The reaction mixture was stirred for 20 hours at ambient temperature. The reaction mixture was then diluted with more dichloromethane (100 ml) and washed successively with water, aqueous hydrochloric acid (2M), and aqueous sodium hydrogen carbonate (saturated). The organic phase was dried over magnesium sulfate and concentrated to give 3-[2-(2,6-dichloro-pyrid-3-yl)-acetylamino]-pyrazine-2-carboxylic acid methyl ester (1.16 g). $^1$H-NMR (400 MHz, CDCl$_3$): 4.04 (s, 3H), 4.12 (s, 2H), 7.30 (d, 1H), 7.71 (d, 1H), 8.42 (d, 1H), 8.59 (d, 1H), 10.91 (s, 1H) ppm.

The following compounds were made by analogous methods:

3-[2-(3,5-Dichloro-pyrid-4-yl)-acetylamino]-pyrazine-2-carboxylic acid methyl ester from (3,5-dichloro-pyrid-4-yl)-acetic acid (prepared according to WO 99/32449). $^1$H-NMR (400 MHz, CDCl$_3$): 4.04 (s, 3H), 4.43 (s, 2H), 8.43 (d, 1H), 8.55 (s, 2H), 8.60 (d, 1H) ppm.

3-[2-(2,5-Dichloro-pyrid-4-yl)-acetylamino]-pyrazine-2-carboxylic acid methyl ester from (2,5-dichloro-pyrid-4-yl)-acetic acid (prepared according to WO 99/32449). $^1$H-NMR (400 MHz, CDCl$_3$): 4.07 (s, 3H), 4.17 (s, 2H), 8.37 (s, 1H), 8.41 (s, 1H), 8.44 (d, 1H), 8.59 (d, 1H) ppm.

3-[2-(2,4-Dichloro-pyrid-3-yl)-acetylamino]-pyrazine-2-carboxylic acid methyl ester from (2,4-dichloro-pyrid-3-yl)-acetic acid (prepared according to WO 99/32449), was used without further purification.

3-[2-(4,6-Dichloro-pyrid-3-yl)-acetylamino]-pyrazine-2-carboxylic acid methyl ester from (4,6-dichloro-pyrid-3-yl)-acetic acid (commercially available). $^1$H-NMR (400 MHz, CDCl$_3$): 4.05 (s, 3H), 4.17 (s, 2H), 7.46 (s, 1H), 8.37 (s, 1H), 8.43 (d, 1H), 8.60 (d, 1H) ppm.

Example 1.6

Preparation of 7-(2,6-dichloro-pyrid-3-yl)-8-hydroxy-5H-pyrido[2,3-b]pyrazin-6-one (Compound No. A13 of Table A)

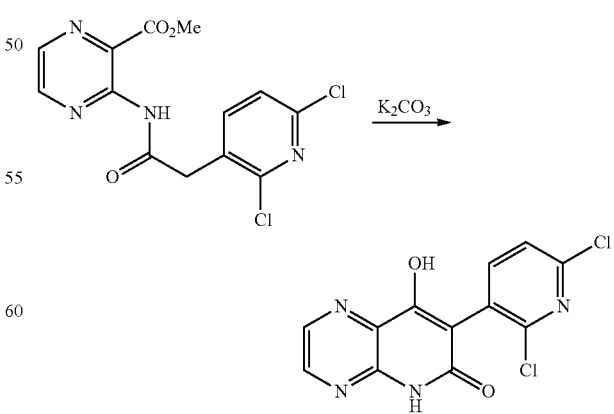

A mixture of 3-[2-(2,6-dichloro-pyrid-3-yl)-acetylamino]-pyrazine-2-carboxylic acid methyl ester (Example 1.5) (1.16 g) and potassium carbonate (0.943 g) in dry N,N-dimethylformamide (20 ml) was heated to 100° C. for 3 hours. The reaction mixture was cooled to ambient temperature and diluted with ethyl acetate. The mixture was filtered and the solid was washed with further ethyl acetate. The solid was then suspended in water and the pH of the suspension adjusted to pH 2 by addition of aqueous hydrochloric acid (2M). The aqueous phase was filtered to give Compound No. A13 of Table A as a beige solid which was washed with a small amount of water, followed by diethyl ether and allowed to dry (0.380 g).

The following compounds were made by analogous methods:

7-(3,5-Dichloro-pyrid-4-yl)-8-hydroxy-5H-pyrido[2,3-b]pyrazin-6-one (Compound No. A25 of Table A) from 3-[2-(3,5-dichloro-pyrid-4-yl)-acetylamino]-pyrazine-2-carboxylic acid methyl (Example 1.5).

7-(2,5-Dichloro-pyrid-4-yl)-8-hydroxy-5H-pyrido[2,3-b]pyrazin-6-one (Compound No. A22 of Table A) from 3-[2-(2,5-dichloro-pyrid-4-yl)-acetylamino]-pyrazine-2-carboxylic acid methyl (Example 1.5).

7-(2,4-Dichloro-pyrid-3-yl)-8-hydroxy-5H-pyrido[2,3-b]pyrazin-6-one (Compound No. A24 of Table A) from 3-[2-(2,4-dichloro-pyrid-3-yl)-acetylamino]-pyrazine-2-carboxylic acid methyl ester (Example 1.5).

7-(4,6-Dichloro-pyrid-3-yl)-8-hydroxy-5H-pyrido[2,3-b]pyrazin-6-one (Compound No. A26 of Table A) from 3-[2-(4,6-dichloro-pyrid-3-yl)-acetylamino]-pyrazine-2-carboxylic acid methyl ester (Example 1.5).

Example 1.7

Preparation of 2,2-dimethyl-propionic acid 7-(2,6-dichloro-pyrid-3-yl)-6-oxo-5,6-dihydro-pyrido[2,3-b]pyrazin-8-yl ester (Compound No. A14 of Table A)

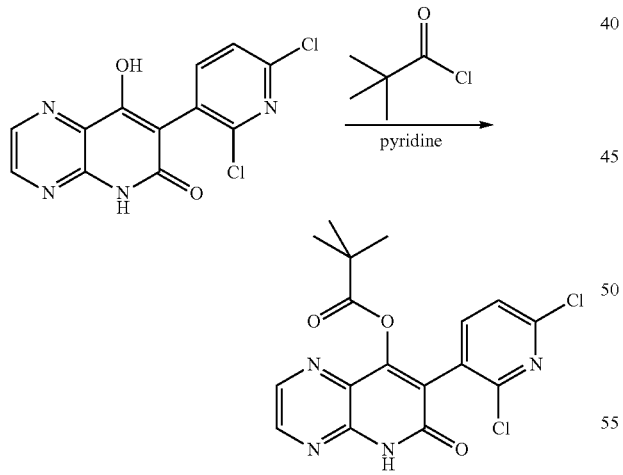

Pivaloyl chloride (0.096 ml) was added dropwise to a solution of 7-(2,6-dichloro-pyrid-3-yl)-8-hydroxy-5H-pyrido[2,3-b]pyrazin-6-one (Example 1.6) (0.20 g) and pyridine (0.068 ml) in dichloromethane (5 ml) at ambient temperature. The reaction mixture was stirred at ambient temperature for 1 hour and was then diluted with more dichloromethane. The organic phase was washed with aqueous sodium hydrogen carbonate (saturated) and brine, dried over magnesium sulfate, and concentrated. The residue was purified by column chromatography on silica gel (eluent: ethyl acetate/hexane 2:1) to give Compound No. A14 of Table A as a white solid (0.088 g).

The following compounds were made by analogous methods:

2,2-Dimethyl-propionic acid 7-(3,5-dichloro-pyrid-4-yl)-6-oxo-5,6-dihydro-pyrido[2,3-b]pyrazin-8-yl ester (Compound No. A8 of Table A) from 7-(3,5-dichloro-pyrid-4-yl)-8-hydroxy-5H-pyrido[2,3-b]pyrazin-6-one (Example 1.6).

2,2-Dimethyl-propionic acid 7-(2,5-dichloro-pyrid-4-yl)-6-oxo-5,6-dihydro-pyrido[2,3-b]pyrazin-8-yl ester (Compound No. A23 of Table A) from 7-(2,5-dichloro-pyrid-4-yl)-8-hydroxy-5H-pyrido[2,3-b]pyrazin-6-one (Example 1.6).

2,2-Dimethyl-propionic acid 7-(2,4-dichloro-pyrid-3-yl)-6-oxo-5,6-dihydro-pyrido[2,3-b]pyrazin-8-yl ester (Compound No. A11 of Table A) from 7-(2,4-dichloro-pyrid-3-yl)-8-hydroxy-5H-pyrido[2,3-b]pyrazin-6-one (Example 1.6).

2,2-Dimethyl-propionic acid 7-(4,6-dichloro-pyrid-3-yl)-6-oxo-5,6-dihydro-pyrido[2,3-b]pyrazin-8-yl ester (Compound No. A27 of Table A) from 7-(4,6-dichloro-pyrid-3-yl)-8-hydroxy-5H-pyrido[2,3-b]pyrazin-6-one (Example 1.6).

Example 1.8

Preparation of 2,2-dimethyl-propionic acid 7-(2,6-dichloro-pyrid-3-yl)-5-(2,2-difluoro-ethyl)-6-oxo-5,6-dihydro-pyrido[2,3-b]pyrazin-8-yl ester (Compound No. A16 of Table A)

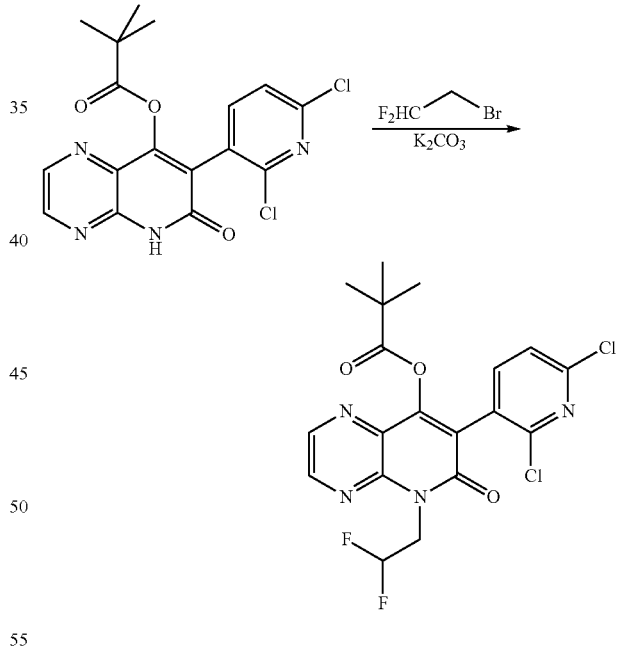

To s suspension of 2,2-dimethyl-propionic acid 7-(2,6-dichloro-pyrid-3-yl)-6-oxo-5,6-dihydro-pyrido[2,3-b]pyrazin-8-yl ester (Example 1.7) (0.064 g) in dry N,N-dimethylformamide (3 ml) was added successively potassium carbonate (0.068 g) and difluoro-ethyl bromide (0.063 g). The reaction mixture was heated in a microwave for 20 minutes at 120° C. The reaction mixture was cooled to ambient temperature, and then diluted with ethyl acetate and water. The phases were separated and organic phase was washed with water and brine, dried over magnesium sulfate, and concentrated to give Compound No. A16 of Table A as a pale yellow solid (0.006 g).

The following compounds were made by analogous methods:

2,2-Dimethyl-propionic acid 7-(3,5-dichloro-pyrid-4-yl)-5-(2,2-difluoro-ethyl)-6-oxo-5,6-dihydro-pyrido[2,3-b]pyrazin-8-yl ester (Compound No. A11 of Table A) from 2,2-dimethyl-propionic acid 7-(3,5-dichloro-pyrid-4-yl)-6-oxo-5,6-dihydro-pyrido[2,3-b]pyrazin-8-yl ester (Example 1.7). 7-(3,5-Dichloro-pyrid-4-yl)-5-(2,2-difluoro-ethyl)-8-hydroxy-5H-pyrido[2,3-b]pyrazin-6-one (Compound No. A12 of Table A) was obtained as a by-product.

7-(2,5-Dichloro-pyrid-4-yl)-5-(2,2-difluoro-ethyl)-8-hydroxy-5H-pyrido[2,3-b]pyrazin-6-one (Compound No. A21 of Table A) was obtained from 2,2-dimethyl-propionic acid 7-(2,5-dichloro-pyrid-4-yl)-6-oxo-5,6-dihydro-pyrido[2,3-b]pyrazin-8-yl ester (Example 1.7) as a by-product.

2,2-Dimethyl-propionic acid 7-(2,4-dichloro-pyrid-3-yl)-5-(2,2-difluoro-ethyl)-6-oxo-5,6-dihydro-pyrido[2,3-b]pyrazin-8-yl ester (Compound No. A18 of Table A) from 2,2-dimethyl-propionic acid 7-(2,4-dichloro-pyrid-3-yl)-6-oxo-5,6-dihydro-pyrido[2,3-b]pyrazin-8-yl ester (Example 1.7).

2,2-Dimethyl-propionic acid 7-(4,6-dichloro-pyrid-3-yl)-5-(2,2-difluoro-ethyl)-6-oxo-5,6-dihydro-pyrido[2,3-b]pyrazin-8-yl ester (Compound No. A20 of Table A) from 2,2-dimethyl-propionic acid 7-(4,6-dichloro-pyrid-3-yl)-6-oxo-5,6-dihydro-pyrido[2,3-b]pyrazin-8-yl ester (Example 1.7). 7-(4,6-Dichloro-pyrid-3-yl)-5-(2,2-difluoro-ethyl)-8-hydroxy-5H-pyrido[2,3-b]pyrazin-6-one (Compound No. A19 of Table A) was obtained as a by-product.

2. Reactions which are Covered by Schemes 1 and 2 where $R^4$ is a 5-Membered Ring

Example 2.1

Preparation of 2-chloro-4-methyl-thiazole acetic acid

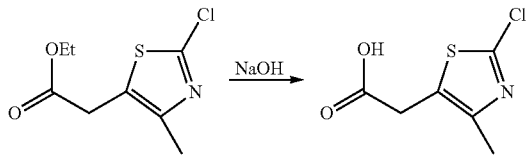

2-Chloro-4-methyl-thiazole acetic acid was prepared by hydrolysis of ethyl 2-chloro-4-methyl-thiazole acetate (which was made as described in EP27019), with aqueous sodium hydroxide (1M) in aqueous methanol (1:1), and was used without further purification.

Example 2.2

Preparation of 3-[2-(2-chloro-4-methyl-thiazol-5-yl)-acetylamino]-pyrazine-2-carboxylic acid methyl ester

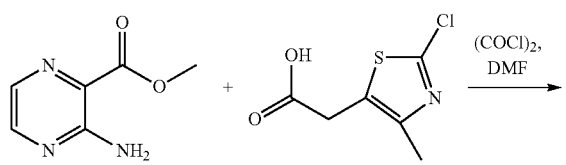

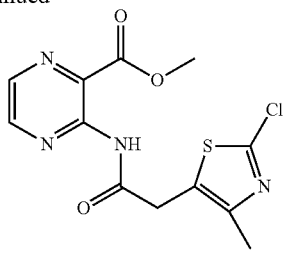

2-Chloro-4-methyl-thiazole acetic acid (Example 2.1) (2.50 g) was dissolved in dichloromethane (70 ml) containing dry N,N-dimethylformamide ("DMF") (3 drops). The reaction mixture was stirred until homogeneous and then cooled to 0° C. Oxalyl chloride (2.66 ml) was added dropwise at 0° C., the reaction mixture was stirred at ambient temperature for 4 hours and then evaporated. The reaction mixture was re-dissolved in acetonitrile (30 ml) and added to 3-amino-pyrazine-2-carboxylic acid methyl ester (1.82 g). The reaction was heated in a microwave to 85° C. for 40 minutes and then cooled to ambient temperature. The reaction mixture was diluted with ethyl acetate and washed with aqueous sodium hydrogen carbonate (saturated), water and aqueous hydrochloric acid (1M) and then water again. The organic layer was dried over magnesium sulfate and concentrated. The residue was purified using column chromatography on silica gel (eluent: hexane/ethyl acetate 1:1) to give 3-[2-(2-chloro-4-methyl-thiazol-5-yl)-acetylamino]-pyrazine-2-carboxylic acid methyl ester (0.98 g). $^1$H-NMR (400 MHz, CDCl$_3$): 2.40 (s, 3H), 4.05 (s, 3H), 4.10 (s, 2H), 8.45 (d, 1H), 8.60 (d, 1H), 10.9 (s, 1H) ppm.

Example 2.3

Preparation of 7-(2-chloro-4-methyl-thiazol-5-yl)-8-hydroxy-5H-pyrido[2,3-b]pyrazin-6-one (Compound No. B1 of Table B)

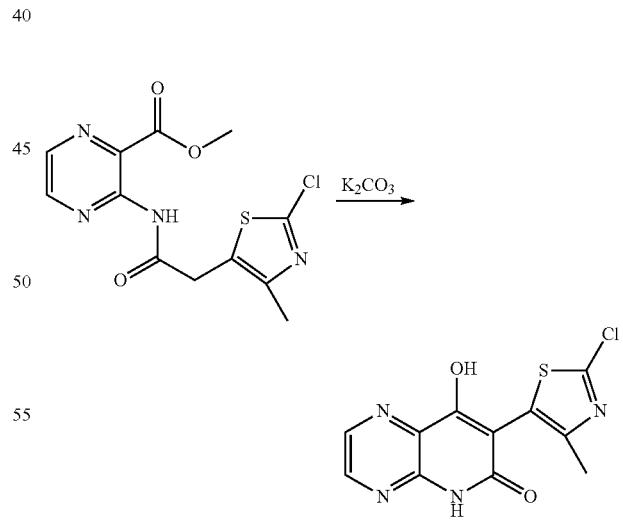

3-[2-(2-Chloro-4-methyl-thiazol-5-yl)-acetylamino]-pyrazine-2-carboxylic acid methyl ester (Example 2.2) (1.020 g) was heated to 110° C. with potassium carbonate (1.08 g) in dry N,N-dimethylformamide (30 ml) for 3 hours. The reaction mixture was allowed to cool to ambient temperature, diluted with water and the mixture extracted with ethyl acetate. The aqueous fraction was acidified to pH 3 by addition of concentrated hydrochloric acid (36% by weight in water) and then extracted again with ethyl acetate. The organic fraction was washed with water, dried over magnesium sulfate, and concentrated to give Compound No. B1 of Table B (0.61 g).

Example 2.4

Preparation of isobutyric acid 7-(2-chloro-4-methyl-thiazol-5-yl)-6-oxo-5,6-dihydro-pyrido[2,3-b]pyrazin-8-yl ester (Compound No. B9 of Table B)

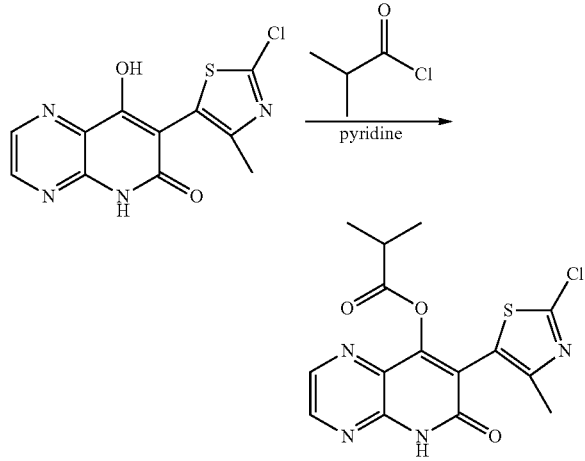

7-(2-Chloro-4-methyl-thiazol-5-yl)-8-hydroxy-5H-pyrido[2,3-b]pyrazin-6-one (Example 2.3) (0.30 g), isobutyryl chloride (0.13 ml), and pyridine (0.10 ml) were stirred in dichloromethane (15 ml) at ambient temperature for 2 hours. The reaction mixture was washed successively with aqueous hydrochloric acid (1M), aqueous sodium hydrogen carbonate (saturated) and water. The organic fraction was dried over magnesium sulfate and concentrated to give Compound No. B9 of Table B (0.220 g).

The following compound was made by an analogous method:

Isobutyric acid 6-hydroxy-7-(3-trifluoromethyl-isoxazol-5-yl)-pyrido[2,3-b]pyrazin-8-yl ester (Compound No. B7 from Table B) from 8-hydroxy-7-(3-trifluoro-methyl-isoxazol-5-yl)-5H-pyrido[2,3-b]pyrazin-6-one (Example 6.5).

Example 2.5

Preparation of isobutyric acid 7-(2-chloro-4-methyl-thiazol-5-yl)-5-methyl-6-oxo-5,6-dihydro-pyrido[2,3-b]pyrazin-8-yl ester (Compound No. B2 of Table B)

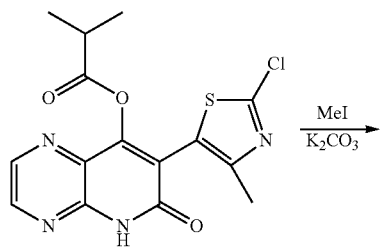

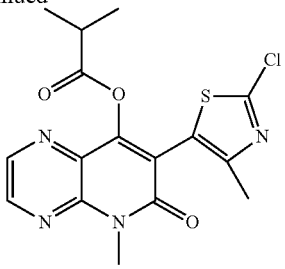

Isobutyric acid 7-(2-chloro-4-methyl-thiazol-5-yl)-6-oxo-5,6-dihydro-pyrido[2,3-b]pyrazin-8-yl ester (Example 2.4) (0.10 g), methyl iodide (0.18 ml) and potassium carbonate (0.075 g) were heated in acetonitrile (4 ml) in a microwave to 100° C. for 10 minutes. The reaction mixture was allowed to cool to ambient temperature and then diluted with ethyl acetate and water. The phases were separated and the organic phase was washed with water, aqueous sodium hydrogen carbonate (saturated) and brine, dried over magnesium sulfate and concentrated to give Compound No. B2 of Table B (0.078 g).

The following compound was made by an analogous method:

Isobutyric acid 5-methyl-6-oxo-7-(3-trifluoromethyl-isoxazol-5-yl)-5,6-dihydro-pyrido[2,3-b]pyrazin-8-yl ester (Compound No. B8 from Table B) from isobutyric acid 6-hydroxy-7-(3-trifluoromethyl-isoxazol-5-yl)-pyrido[2,3-b]pyrazin-8-yl ester (Example 2.4).

3. Example of a Reaction Covered by Scheme 6

Example 3.1

Preparation of methanesulfonic acid 7-(3,5-dichloro-pyrid-2-yl)-6-oxo-5,6-dihydro-pyrido[2,3-b]pyrazin-8-yl ester (Compound No. A4 of Table A)

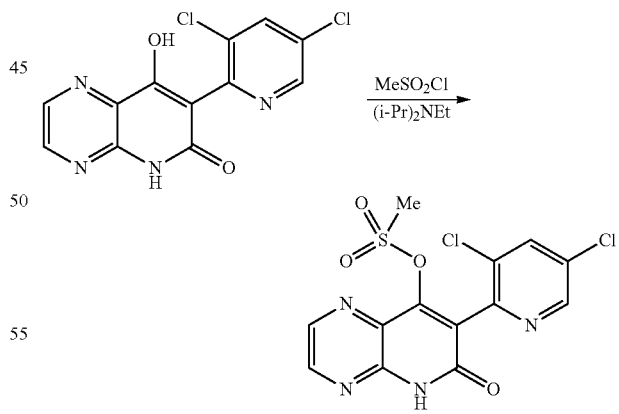

To a suspension of 7-(3,5-dichloro-pyrid-2-yl)-pyrido[2,3-b]pyrazine-6,8-diol (Example 1.2) (0.20 g) and N-ethyl-diisopropylamine (0.126 g) in dry dichloromethane (15 ml) was added methane sulfonyl chloride (0.074 g). The reaction mixture was stirred at ambient temperature for one hour and then stored at ambient temperature for 16 hours. The reaction mixture was diluted with aqueous hydrochloric acid (1M). The phases were separated and the organic layer was concentrated. The residue was purified by reverse phase HPLC to give Compound No. A4 of Table A as a pale brown solid (0.055 g).

4. Examples of Reactions Covered by Scheme 7

Example 4.1

Preparation of 3-bromomethyl-2,6-dichloro-pyridine

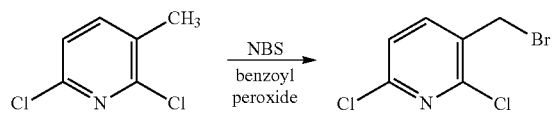

2,6-Dichloro-3-methyl-pyridine (3.6 g), N-bromosuccinimide ("NBS") (3.98 g), benzoyl peroxide (catalytic amount) and carbon tetrachloride (25 ml) were heated to reflux and a 500 watt tungsten halogen lamp was used to initiate the reaction. Reflux was continued for 8 hours. The reaction mixture was filtered to remove the solids and the filtrate concentrated to yield a mixture of 3-bromomethyl-2,6-dichloro-pyridine, 3,3-dibromomethyl-2,6-dichloro-pyridine, and 2,6-dichloro-3-methyl-pyridine (58:26:16). The mixture was used without purification for the next step.

Example 4.2

Preparation of (2,6-dichloro-pyrid-3-yl)-acetonitrile

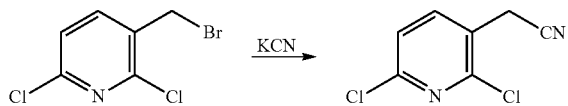

Potassium cyanide (1.0 g) was dissolved in water by heating to 40° C. A mixture of 3-bromomethyl-2,6-dichloro-pyridine, 3,3-dibromomethyl-2,6-dichloro-pyridine, and 2,6-dichloro-3-methyl-pyridine (Example 4.1) (3.2 g) suspended in ethanol (20 ml) was added dropwise at 40° C. over a period of 30 minutes. The reaction mixture was heated to reflux for 3 hours. The reaction mixture was cooled to 40° C. and another equivalent of potassium cyanide was added. The reaction mixture was heated to reflux for a further 3 hours and then stored at ambient temperature for 16 hours. The reaction mixture was filtered to remove the solids and the solids were washed with ethyl acetate. The combined filtrates were concentrated. The residue was diluted with ethyl acetate. The organic solution washed with aqueous sodium hydrogen carbonate (saturated) and brine, dried over magnesium sulfate, and concentrated. This residue was purified by column chromatography on silica gel (eluent: ethyl acetate/hexane from 3:100 to 1:1) to give slightly impure (2,6-dichloro-pyrid-3-yl)-acetonitrile (1.5 g) which solidified on standing. This material was used without further purification. $^1$H-NMR (400 MHz, CDCl$_3$): 3.83 (s, 2H), 7.37 (d, 1H), 7.85 (d, 1H) ppm.

Example 4.3

Preparation of (2,6-dichloro-pyrid-3-yl)-acetic acid

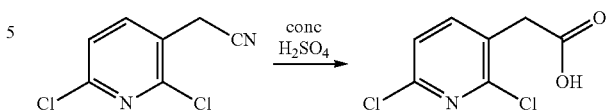

(2,6-Dichloro-pyrid-3-yl)-acetonitrile (Example 4.2) (1.5 g) was dissolved in a 1:1 mixture of water and concentrated sulfuric acid. The reaction mixture was heated to reflux for 3 hours, then allowed to cool to ambient temperature and stored at ambient temperature for 16 hours. The reaction mixture was diluted with dichloromethane and the phases were separated. The organic phase was dried over magnesium sulfate and concentrated to give (2,6-dichloro-pyrid-3-yl)-acetic acid as a cream-coloured solid (1.174 g). $^1$H-NMR (400 MHz, CDCl$_3$): 3.78 (s, 2H), 7.40 (d, 1H), 7.80 (d, 1H) ppm.

5. Examples of Reactions Covered by Scheme 8

Example 5.1

Preparation of (3,5-dichloro-pyrid-2-yl)-acetic acid

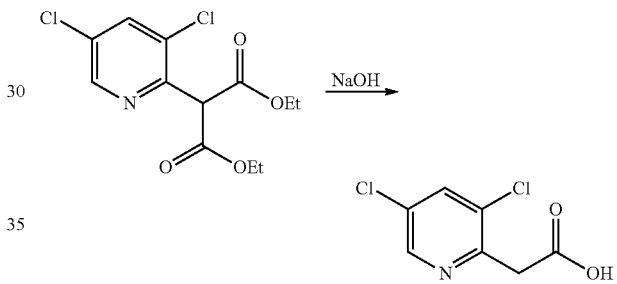

To a solution of 2-(3,5-dichloro-pyrid-2-yl)-malonic acid diethyl ester (118.5 g) (prepared as described in WO 07/101,859) in methanol (1 ml) was added aqueous sodium hydroxide (47 g dissolved in 300 ml water). The reaction mixture was heated to 80° C. for 1 hour. The methanol was evaporated and the pH of the aqueous phase adjusted to pH 4 by addition of glacial acetic acid and then extracted with ethyl acetate. The combined organic phases were dried over magnesium sulfate and concentrated to give (3,5-dichloro-pyrid-2-yl)-acetic acid as an off-white solid (50 g). $^1$H-NMR (400 MHz, CDCl$_3$): 4.04 (s, 2H), 7.81 (d, 1H), 8.45 (d, 1H) ppm.

6. Examples of Reactions Covered by Scheme 9

Example 6.1

Preparation of 3-(3-oxo-butyrylamino)-pyrazine-2-carboxylic acid methyl ester

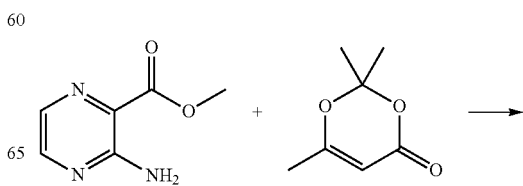

-continued

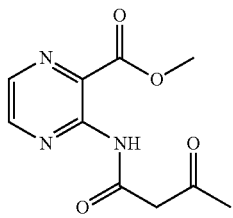

3-Aminopyrazine-2-carboxylic acid methyl ester (12 g) and 2,2,6-trimethyl-[1,3]dioxin-4-one (15.6 ml) were heated to reflux for 6 hours. The reaction mixture was concentrated. The residue was purified by column chromatography on silica gel (eluent: ethyl acetate/hexane 4:1, then ethyl acetate) to give 3-(3-oxo-butyrylamino)-pyrazine-2-carboxylic acid methyl ester as a beige solid (15 g). $^1$H-NMR (400 MHz, CDCl$_3$): 2.33 (s, 3H), 3.91 (s, 2H), 4.05 (s, 3H), 8.40 (d, 1H), 8.51 (d, 1H), 10.06 (s, 1H) ppm.

Example 6.2

Preparation of 1-(6,8-dihydroxy-pyrido[2,3-b]pyrazin-7-yl)-ethanone

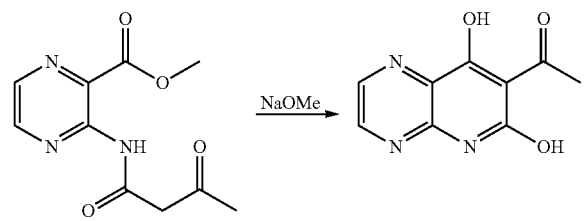 [SMILES: COC(=O)c1nccnc1NC(=O)CC(C)=O ; CC(=O)c1c(O)nc2nccnc2c1O ; "NaOMe"]

3-(3-Oxo-butyrylamino)-pyrazine-2-carboxylic acid methyl ester (Example 6.1) (15 g) in methanol (80 ml) was added to a suspension of sodium methoxide (7.2 g) in methanol (80 ml). The suspension was heated to reflux for 2 hours and then stored for 16 hours at ambient temperature. The mixture was filtered and the filtrate was acidified to pH 1 by addition of concentrated hydrochloric acid (36% by weight in water) and then filtered again. The solid was washed with water and then diethyl ether to give 1-(6,8-dihydroxy-pyrido[2,3-b]pyrazin-7-yl)-ethanone (10.1 g). $^1$H-NMR (400 MHz, d$_6$-DMSO): 2.70 (s, 3H), 8.60 (d, 1H), 8.71 (d, 1H), 12.2 (s, 1H), 16.25 (s, 1H) ppm.

Example 6.3

Preparation of 8-hydroxy-7-((Z)-4,4,4-trifluoro-1-hydroxy-3-oxo-but-1-enyl)-5H-pyrido[2,3-b]pyrazin-6-one

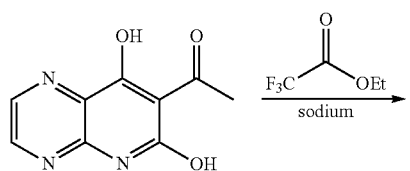

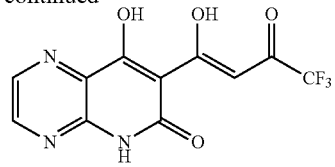

To a suspension of 1-(6,8-dihydroxy-pyrido[2,3-b]pyrazin-7-yl)-ethanone (Example 6.2) (1.0 g) in ethyl trifluoroacetate (14 ml) and was added sodium (0.56 g) in portions. The reaction mixture was heated to reflux for 4 hours. The reaction mixture was stored at ambient temperature for 16 hours and then poured into aqueous acetic acid (1:1). The solid was isolated by filtration and washed with water, ethanol, ethyl acetate and diethyl ether and then dried to give a yellow solid (0.760 g). The solid was heated to reflux for a further two days in ethyl trifluoroacetate (14 ml) and sodium (0.56 g) and worked up similarly to give a darker yellow solid (0.515 g), which in turn was heated to reflux again in ethyl trifluoroacetate (7 ml) and sodium (0.290 g) and worked up similarly to give 8-hydroxy-7-(Z)-4,4,4-trifluoro-1-hydroxy-3-oxo-but-1-enyl)-5H-pyrido[2,3-b]pyrazin-6-one as a dark yellow solid (0.190 g). $^1$H-NMR (400 MHz, d$_6$-DMSO): 7.30 (s, 1H), 8.45 (d, 1H), 8.51 (d, 1H), 11.36 (s, 1H), 11.97 (s, 1H) ppm.

Example 6.4

Preparation of 4,4,4-trifluoro-1-(8-hydroxy-6-oxo-5,6-dihydro-pyrido[2,3-b]pyrazin-7-yl)-butane-1,3-dione 3-oxime

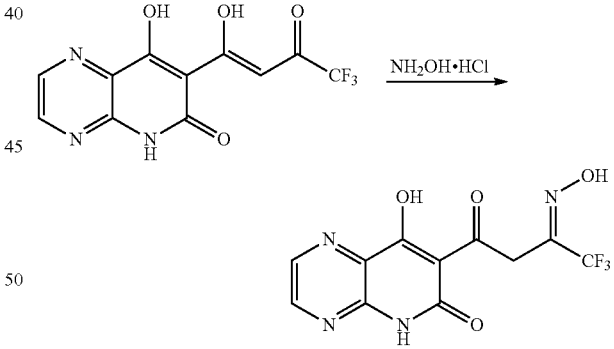

To a suspension of 4,4,4-trifluoro-1-(8-hydroxy-6-oxo-5,6-dihydro-pyrido[2,3-b]pyrazin-7-yl)-butane-1,3-dione (Example 6.3) (0.170 g) in ethanol (2 ml) was added hydroxylamine hydrochloride (0.050 g). The reaction mixture was heated to reflux for 4 hours and was then stored at ambient temperature for 16 hours. The solid was isolated by filtration and washed with ethanol, ethyl acetate, and diethyl ether and dried to give 4,4,4-trifluoro-1-(8-hydroxy-6-oxo-5,6-dihydro-pyrido[2,3-b]pyrazin-7-yl)-butane-1,3-dione 3-oxime as a brown solid (0.078 g). $^1$H-NMR (400 MHz, d$_6$-DMSO): 3.61 (d, 1H), 3.86 (d, 1H), 8.57 (d, 1H), 8.67 (d, 1H), 12.35 (s, 1H) ppm.

Example 6.5

Preparation of 8-hydroxy-7-(3-trifluoromethyl-isoxazol-5-yl)-5H-pyrido[2,3-b]pyrazin-6-one (Compound No. B10 of Table B)

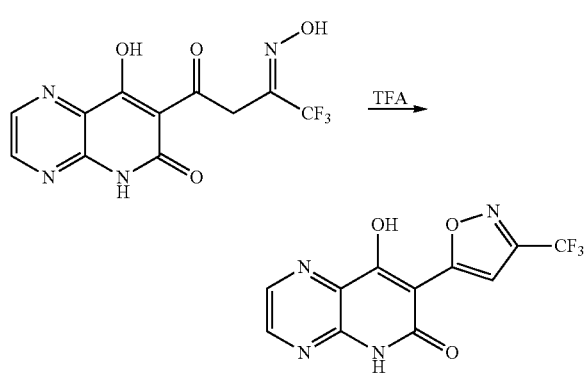

A suspension of 4,4,4-trifluoro-1-(8-hydroxy-6-oxo-5,6-dihydro-pyrido[2,3-b]pyrazin-7-yl)-butane-1,3-dione 3-oxime (Example 6.4) (0.068 g) in trifluoroacetic acid ("TFA") (0.5 ml) was heated to reflux for 7 hours. The solid was isolated by filtration and washed with diethyl ether and then dried. The solid was heated to reflux again in trifluoroacetic acid ("TFA") (2.0 ml) for 2 days and worked up similarly to give Compound No. B10 of Table B (0.050 g).

Example 6.6

Alternative preparation of isobutyric acid 6-hydroxy-7-(3-trifluoromethyl-isoxazol-5-yl)-pyrido[2,3-b]pyrazin-8-yl ester (Compound No. B7 of Table B)

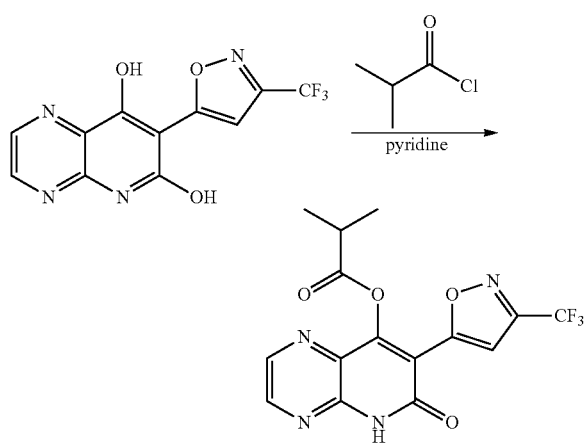

To a solution of 8-hydroxy-7-(3-trifluoromethyl-isoxazol-5-yl)-5H-pyrido[2,3-b]pyrazin-6-one (Example 6.5) (0.037 g) and pyridine (0.1 ml) in dichloromethane (2 ml) was added dropwise isobutyryl chloride (0.05 ml). The reaction mixture was stirred at ambient temperature for 6 hours and stored at ambient temperature for 16 hours. The reaction mixture was diluted with ethyl acetate, and the organic phase was washed successively with water, aqueous sodium hydrogen carbonate (saturated) and brine. The organic phase was dried over magnesium sulfate and concentrated to give Compound No. B7 of Table B as a pale yellow solid (0.038 g).

Example 6.7

Alternative preparation of isobutyric acid 5-methyl-6-oxo-7-(3-trifluoromethyl-isoxazol-5-yl)-5,6-dihydro-pyrido[2,3-b]pyrazin-8-yl ester (Compound No. B8 of Table B)

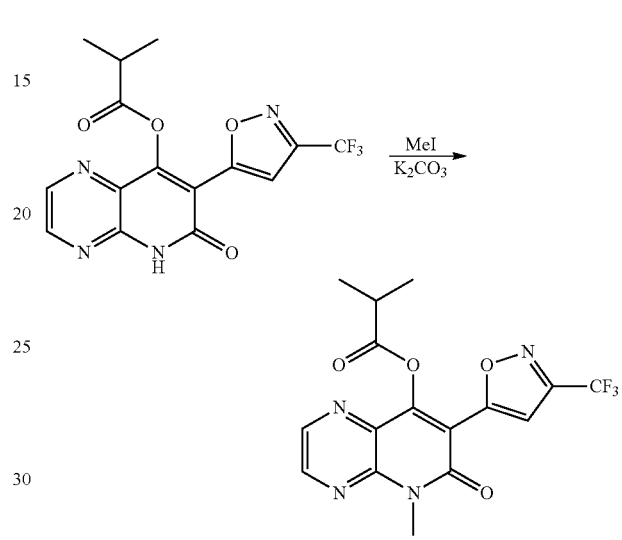

Potassium carbonate (0.023 g) and methyl iodide (0.01 ml) were added to isobutyric acid 6-hydroxy-7-(3-trifluoromethyl-isoxazol-5-yl)-pyrido[2,3-b]pyrazin-8-yl ester (Example 6.6) (0.030 g) in acetonitrile (1.5 ml). The reaction mixture was heated in a microwave to 100° C. for 10 minutes. The reaction mixture was diluted with ethyl acetate and water. The phases were separated. The organic phase was washed with water and brine, dried over magnesium sulfate and concentrated. The residue was purified by column chromatography on silica gel (eluent: ethyl acetate/hexane 1:2 to 1:1) to give Compound No. B8 of Table B (0.025 g) as a colourless oil that solidified on standing.

7. Examples of Reactions Covered by Scheme 10

Example 7.1

Preparation of 8-hydroxy-6-oxo-5,6-dihydro-pyrido[2,3-b]pyrazine-7-carboxylic acid methyl ester

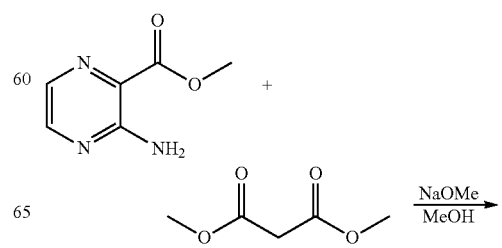

-continued

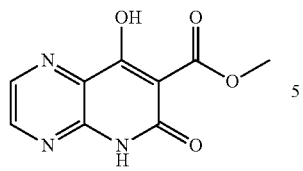

Sodium methoxide (6.5 ml) (30% by weight in methanol) was dissolved in methanol (75 ml) at room temperature. Dimethyl malonate (3.7 ml) was added dropwise at ambient temperature over a period of 20 minutes and the reaction stirred at ambient temperature for 1 hour. Methyl 3-aminopyrazine-2-carboxylate (5.0 g) was added in portions at ambient temperature over a period of 40 minutes. The reaction mixture was heated to reflux for 3 days, and then allowed to cool. The solvent was concentrated. The residue was dissolved in water and acidified with concentrated hydrochloric acid (36% by weight in water). The precipitate was isolated, washed with water, methanol and ethyl acetate, and dried under high vacuum to give 8-hydroxy-6-oxo-5,6-dihydro-pyrido[2,3-b]pyrazine-7-carboxylic acid methyl ester as a beige solid (4.16 g). $^1$H-NMR (d$_6$-DMSO): 3.80 (s, 3H), 8.59 (s, 1H), 8.70 (s, 1H) ppm.

Example 7.2

Preparation of 8-isobutyryloxy-6-oxo-5,6-dihydro-pyrido[2,3-b]pyrazine-7-carboxylic acid methyl ester

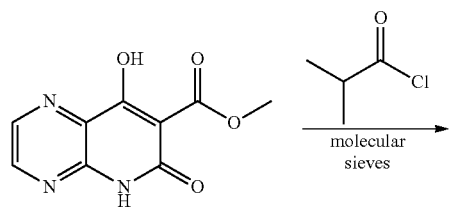

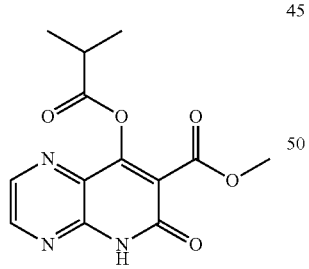

To a suspension of 8-hydroxy-6-oxo-5,6-dihydro-pyrido[2,3-b]pyrazine-7-carboxylic acid methyl ester (Example 7.1) in 1,2-dichloro-ethane (9 ml) was added powdered molecular sieves (4A) followed by dropwise addition of isobutyryl chloride (0.048 ml). The reaction mixture was heated to reflux for 5 hours, cooled to ambient temperature and filtered. The filtrate was concentrated to give 8-isobutyryloxy-6-oxo-5,6-dihydro-pyrido[2,3-b]pyrazine-7-carboxylic acid methyl ester as a light brown solid (0.166 g) which was used without further purification.

Example 7.3

Preparation of 8-isobutyryloxy-5-methyl-6-oxo-5,6-dihydro-pyrido[2,3-b]pyrazine-7-carboxylic acid methyl ester

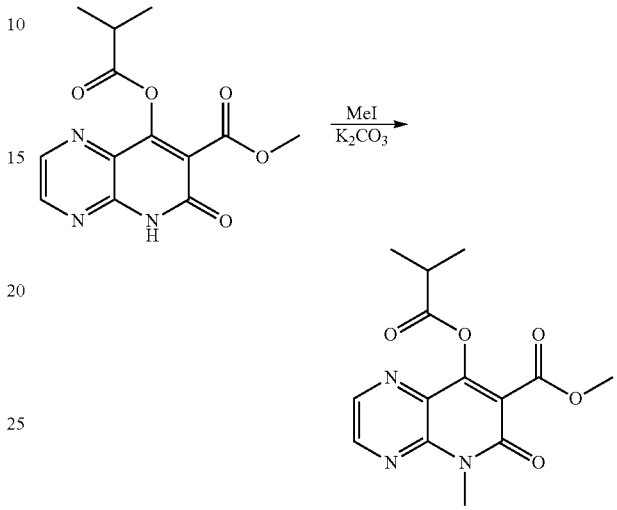

To a suspension of 8-isobutyryloxy-6-oxo-5,6-dihydro-pyrido[2,3-b]pyrazine-7-carboxylic acid methyl ester (0.422 g) (Example 7.2) in acetonitrile (12 ml) was added potassium carbonate (0.401 g) followed by methyl iodide (0.30 ml). The reaction mixture was heated to 100° C. for 10 minutes in a microwave, and then cooled to ambient temperature. The reaction mixture was diluted with ethyl acetate and water. The phases were separated. The organic phase was washed with water and brine, dried over magnesium sulfate and concentrated. The residue was purified by column chromatography on silica gel (eluent: ethyl acetate/hexane 1:2 to 1:1) to give 8-isobutyryloxy-5-methyl-6-oxo-5,6-dihydro-pyrido[2,3-b]pyrazine-7-carboxylic acid methyl ester as an orange oil (0.418 g). $^1$H-NMR (400 MHz, CDCl$_3$): 1.36 (d, 6H), 2.95 (sept, 1H), 3.79 (s, 3H), 3.94 (s, 3H), 8.49 (d, 1H), 8.59 (d, 1H) ppm.

Example 7.4

Preparation of 8-hydroxy-5-methyl-7-(3-methyl-1,2,4-oxadiazol-5-yl)-5H-pyrido[2,3-b]pyrazin-6-one (Compound No. B5 of Table 5)

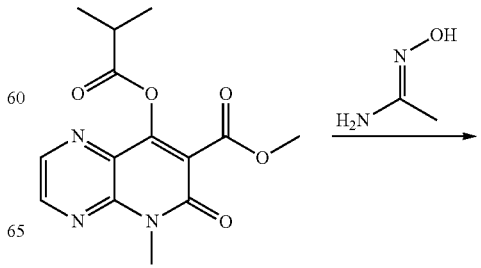

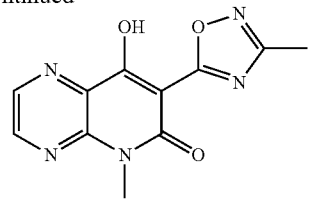

To a solution of 8-isobutyryloxy-5-methyl-6-oxo-5,6-dihydro-pyrido[2,3-b]pyrazine-7-carboxylic acid methyl ester (Example 7.3) (0.10 g) in toluene (4 ml) was added N-hydroxy-acetamidine (0.025 g). The reaction mixture was heated to reflux for 16 hours. The reaction mixture was cooled to ambient temperature and the solid was isolated by filtration and dried to give Compound No. B5 of Table 5 (0.050 g).

Example 7.5

Preparation of isobutyric acid 5-methyl-7-(3-methyl-1,2,4-oxadiazol-5-yl)-6-oxo-5,6-dihydro-pyrido[2,3-b]pyrazin-8-yl ester (Compound No. B6 of Table B)

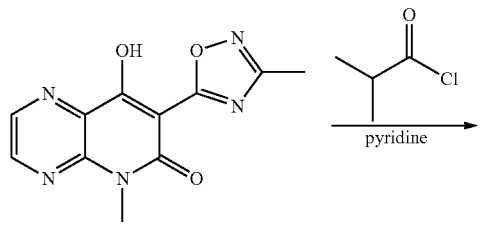

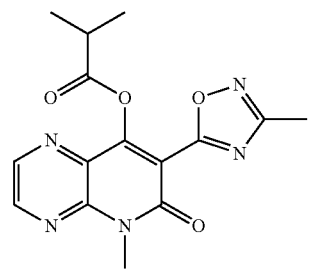

To a solution of 8-hydroxy-5-methyl-7-(3-methyl-1,2,4-oxadiazol-5-yl)-5H-pyrido[2,3-b]pyrazin-6-one (Example 7.4) (0.044 g) and pyridine (0.018 ml) in dichloromethane (1 ml) was added dropwise isobutyryl chloride (0.022 ml). The reaction mixture was stirred at ambient temperature for 4 hours and then stored at ambient temperature for 16 hours. The reaction mixture was diluted with more dichloromethane and the mixture was washed successively with aqueous sodium hydrogen carbonate (saturated), aqueous ammonium chloride (saturated) and brine. The organic fraction was dried over magnesium sulfate and concentrated. The residue was purified by column chromatography on silica gel (eluent: ethyl acetate/hexane 1:1) to give Compound No. B6 of Table 6 as a pale yellow solid (0.020 g).

TABLE A

Compounds of formula (A), where $R^3$, $R^4$ and $R^5$ have the values as described in the table below and $R^4$ is a 6-membered ring.

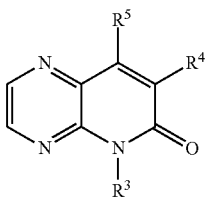

(A)

| Comp No. | $R^3$ | $R^4$ | $R^5$ | $^1$H-NMR (400 MHz, CDCl$_3$ except where indicated; chemical shifts in ppm) |
|---|---|---|---|---|
| A1 | H | 3,5-dichloro-pyrid-2-yl- | HO— | DMSO-d6: 8.03 (d, 1H), 8.23 (d, 1H), 8.28 (d, 1H), 8.51 (d, 1H), 10.35 (s, 1H). |
| A2 | Me | 3,5-dichloro-pyrid-2-yl- | EtO(CO)O— | 1.34 (t, 3H), 3.88 (s, 3H), 4.31 (q, 2H), 7.88 (d, 1H), 8.55 (d, 1H), 8.59 (d, 1H), 8.65 (d, 1H). |
| A3 | H | 3,5-dichloro-pyrid-2-yl- | EtO(CO)O— | 1.34 (t, 3H), 4.32 (q, 2H), 7.88 (d, 1H), 8.59 (m, 3H), 9.84 (s, 1H). |
| A4 | H | 3,5-dichloro-pyrid-2-yl- | Me(SO$_2$)O— | 3.50 (s, 3H), 7.90 (d, 1H), 8.64 (m, 3H). |
| A5 | H | 3,5-dichloro-pyrid-2-yl- | i-Pr—(CO)O— | DMSO-d6: 1.10 (d, 6H), 2.84 (m, 1H), 7.40 (t, 2H), 8.60 (d, 1H), 8.74 (d, 1H), 13.0 (s, 1H). |
| A6 | Et | 3,5-dichloro-pyrid-2-yl- | i-Pr—(CO)O— | 1.16 (d, 6H), 1.35 (t, 3H), 4.55 (q, 2H), 7.86 (d, 1H), 8.48 (d, 1H), 8.58 (d, 1H), 8.61 (d, 1H). |
| A7 | Me | 3,5-dichloro-pyrid-2-yl- | i-Pr—(CO)O— | 1.10 (s, 3H), 1.14 (s, 3H), 2.64 (m, 1H), 3.88 (s, 3H), |

TABLE A-continued

Compounds of formula (A), where $R^3$, $R^4$ and $R^5$ have the values as described in the table below and $R^4$ is a 6-membered ring.

(A)

| Comp No. | $R^3$ | $R^4$ | $R^5$ | $^1$H-NMR (400 MHz, CDCl$_3$ except where indicated; chemical shifts in ppm) |
|---|---|---|---|---|
| | | | | 7.78 (d, 1H), 8.50 (d, 1H), 8.61 (d, 1H), 8.63 (d, 1H). |
| A8 | H | 3,5-dichloro-pyrid-4-yl- | t-Bu—(CO)O— | 1.18 (s, 9H), 8.57 (d, 1H), 8.61 (d, 1H), 8.62 (s, 2H), 10.31 (s, 1H). |
| A9 | Me | 3,5-dichloro-pyrid-4-yl- | t-Bu—(CO)O— | 1.17 (s, 9H), 3.88 (s, 3H), 8.53 (d, 1H), 8.61 (s, 2H), 8.64 (d, 1H). |
| A10 | Et | 3,5-dichloro-pyrid-4-yl- | t-Bu—(CO)O— | 1.17 (s, 9H), 1.37 (t, 3H), 4.59 (q, 2H), 8.52 (d, 1H), 8.60 (s, 2H), 8.63 (d, 1H). |
| A11 | F$_2$HC—H$_2$C— | 3,5-dichloro-pyrid-4-yl- | t-Bu—(CO)O— | 1.18 (s, 9H), 4.98 (dt, 2H), 6.24 (tt, 1H), 8.58 (d, 1H), 8.62 (s, 2H), 8.64 (d, 1H). |
| A12 | F$_2$HC—H$_2$C— | 3,5-dichloro-pyrid-4-yl- | HO— | 4.93 (dt, 2H), 6.24 (tt, 1H), 8.54 (d, 1H), 8.62 (s, 2H), 8.76 (d, 1H). |
| A13 | H | 2,6-dichloro-pyrid-3-yl- | HO— | CD$_3$OD: 7.51 (d, 1H), 7.83 (d, 1H), 8.57 (d, 1H), 8.65 (d, 1H). |
| A14 | H | 2,6-dichloro-pyrid-3-yl- | t-Bu—(CO)O— | 1.22 (s, 9H), 7.37 (d, 1H), 7.63 (d, 1H), 8.55 (d, 1H), 8.58 (d, 1H), 10.05 (s, 1H). |
| A15 | Me | 2,6-dichloro-pyrid-3-yl- | t-Bu—(CO)O— | 1.21 (s, 9H), 3.86 (s, 3H), 7.36 (d, 1H), 7.60 (d, 1H), 8.51 (d, 1H), 8.62 (d, 1H). |
| A16 | F$_2$HC—H$_2$C— | 2,6-dichloro-pyrid-3-yl- | t-Bu—(CO)O— | 1.22 (s, 9H), 4.95 (dt, 2H), 6.24 (tt, 1H), 7.37 (d, 1H), 7.62 (d, 1H), 8.57 (d, 1H), 8.61 (d, 1H). |
| A17 | H | 2,4-dichloro-pyrid-3-yl- | t-Bu—(CO)O— | 1.18 (s, 9H), 7.42 (d, 1H), 8.37 (d, 1H), 8.56 (d, 1H), 8.58 (d, 1H), 9.74 (s, 1H). |
| A18 | F$_2$HC—H$_2$C— | 2,4-dichloro-pyrid-3-yl- | t-Bu—(CO)O— | 1.18 (s, 9H), 4.98 (dt, 2H), 6.25 (tt, 1H), 7.42 (d, 1H), 8.37 (d, 1H), 8.57 (d, 1H), 8.62 (d, 1H). |
| A19 | F$_2$HC—H$_2$C— | 4,6-dichloro-pyrid-3-yl- | HO— | 4.91 (dt, 2H), 6.22 (tt, 1H), 7.54 (s, 1H), 8.39 (s, 1H), 8.52 (d, 1H), 8.72 (d, 1H). |
| A20 | F$_2$HC—H$_2$C— | 4,6-dichloro-pyrid-3-yl- | t-Bu—(CO)O— | 1.22 (s, 9H), 4.96 (dt, 2H), 6.24 (tt, 1H), 7.54 (s, 1H), 8.29 (s, 1H), 8.57 (d, 1H), 8.62 (d, 1H). |
| A21 | F$_2$HC—H$_2$C— | 2,5-dichloro-pyrid-4-yl- | HO— | 4.91 (m, 2H), 6.23 (tt, 1H), 7.40 (s, 1H), 8.51 (s, 1H), 8.53 (d, 1H), 8.74 (d, 1H). |
| A22 | H | 2,5-dichloro-pyrid-4-yl- | HO— | 7.40 (s, 1H), 8.50 (s, 1H), 8.52 (d, 1H), 8.69 (d, 1H). |
| A23 | H | 2,5-dichloro-pyrid-4-yl- | t-Bu—(CO)O— | 1.22 (s, 9H), 7.29 (s, 1H), 8.51 (s, 1H), 8.56 (m, 2H). |
| A24 | H | 2,4-dichloro-pyrid-3-yl- | HO— | CD$_3$OD: 7.61 (d, 1H), 8.36 (d, 1H), 8.59 (d, 1H), 8.67 (d, 1H). |
| A25 | H | 3,5-dichloro-pyrid-4-yl- | HO— | 8.02 (m, 4H). |
| A26 | H | 4,6-dichloro-pyrid-3-yl- | HO— | 7.53 (s, 1H), 8.39 (s, 1H), 8.52 (d, 1H), 8.67 (d, 1H). |

TABLE A-continued

Compounds of formula (A), where $R^3$, $R^4$ and $R^5$ have the values as described in the table below and $R^4$ is a 6-membered ring.

(A)

| Comp No. | $R^3$ | $R^4$ | $R^5$ | $^1$H-NMR (400 MHz, CDCl$_3$ except where indicated; chemical shifts in ppm) |
|---|---|---|---|---|
| A27 | H | 4,6-dichloro-pyrid-3-yl- | t-Bu—(CO)O— | 7.53 (s, 1H), 8.39 (s, 1H), 8.52 (d, 1H), 8.67 (d, 1H). |

Key:
s = singlet;
d = doublet;
t = triplet;
q = quartet;
dt = double triplet;
tt = triple triplet;
m = multiplet;
Me = methyl;
Et = ethyl;
Pr = propyl;
Bu = butyl.

TABLE B

Compounds of formula (B), where $R^3$, $R^4$ and $R^5$ have the values as described in the table below, and $R^4$ is a 5-membered ring.

(B)

| Comp No. | $R^3$ | $R^4$ | $R^5$ | $^1$H-NMR (400 MHz, CDCl$_3$ except where indicated; chemical shifts in ppm) |
|---|---|---|---|---|
| B1 | H | 2-chloro-4-methyl-thiazol-5-yl- | HO— | (d$_6$-DMSO): 2.25 (s, 3H), 8.25 (d, 1H), 8.65 (d, 1H). |
| B2 | Me | 2-chloro-4-methyl-thiazol-5-yl- | i-Pr—(CO)O— | 1.25 (m, 6H), 2.35 (s, 3H), 2.90 (m, 1H), 3.85 (s, 3H), 8.50 (d, 1H), 8.60 (d, 1H). |
| B3 | Me | 2-chloro-4-methyl-thiazol-5-yl- | t-Bu-(CO)O— | 1.30 (9H, s), 2.30 (3H, s), 3.85 (3H, s), 8.50 (1H, d), 8.60 (1H, d). |
| B4 | Et | 2-chloro-4-methyl-thiazol-5-yl- | t-Bu-(CO)O— | 1.35 (9H, s), 1.40 (3H, t), 2.35 (3H, s), 4.60 (2H, q), 8.50 (1H, d), 8.60 (1H, d). |
| B5 | Me | 3-methyl-1,2,4-oxadiazol-5-yl- | HO— | 2.56 (s, 3H), 3.84 (s, 3H), 8.65 (d, 1H), 8.71(d, 1H). |
| B6 | Me | 3-methyl-1,2,4-oxadiazol-5-yl- | i-Pr—(CO)O— | 1.37 (d, 6H), 2.51 (s, 3H), 2.98 (sept, 1H), 3.86 (s, 3H), 8.55 (d, 1H), 8.66 (d, 1H). |
| B7 | H | 3-trifluoro-methyl-isoxazol-5-yl- | i-Pr—(CO)O— | 1.40 (d, 3H), 1.42 (d, 3H), 3.03 (sept, 1H), 7.52 (s, 1H), 8.62 (m, 2H), 10.47 (s, 1H). |
| B8 | Me | 3-trifluoro-methyl-isoxazol-5-yl- | i-Pr—(CO)O— | 1.40 (d, 6H), 3.02 (sept, 1H), 3.88 (s, 3H), 7.46 (s, 1H), 8.57 (d, 1H), 8.65 (d, 1H). |
| B9 | H | 2-chloro-4-methyl-thiazol-5-yl- | i-Pr—(CO)O— | 1.25 (m, 6H), 2.35 (s, 3H), 2.70 (m, 1H), 8.55 (d, 2H), 10.2 (s, 1H). |
| B10 | H | 3-trifluoro-methyl-isoxazol-5-yl- | HO— | 7.64 (s, 1H), 8.60 (d, 1H), 8.71 (d, 1H). |

Key:
s = singlet;
d = doublet;
t = triplet;
q = quartet;
sept = septet;
m = multiplet;
Me = methyl;
Et = ethyl;
Pr = propyl;
Bu = butyl.

BIOLOGICAL EXAMPLES

Example B1

Herbicidal Action

Seeds of a variety of test species were sown in sterilised standard soil in seed trays each having 96 cells. After cultivation for 8 to 9 days cultivation (post-emergence) under controlled conditions in a climatic chamber (cultivation at 23/17° C., day/night; 13 hours light; 50-60% humidity), the plants were treated with an aqueous spray solution of 1000 mg/l of the active ingredient dissolved in 10% DMSO (dimethyl sulfoxide, CAS RN 67-68-5) as a solvent, equivalent to 1000 g/ha. The plants were grown in the climatic chamber after application at (24/19° C., day/night; 13 hours light; 50-60% humidity) and watered twice daily. After 9 days until the test was evaluated (10=total damage to plant, 0=no damage to plant)

TABLE B1

| | Application post-emergence | | | |
|---|---|---|---|---|
| Comp No. | Rate (g/ha) | STEME | NAAOF | AMARE | SOLNI |
| A2 | | 5 | 0 | 0 | 0 |
| A6 | | 3 | 5 | 2 | 0 |
| A7 | | 7 | 7 | 7 | 0 |
| B2 | | 0 | 5 | 0 | 0 |
| B3 | | 2 | 6 | 0 | 0 |
| B4 | | 2 | 8 | 0 | 3 |
| B5 | | 0 | 0 | 3 | 0 |
| B8 | | 0 | 2 | 0 | 2 |

STEME = *Stellaria media*;
NAAOF = *Nasturtium officinale*;
AMARE = *Amaranthus retroflexus*;
SOLNI = *Solanum nigrum*.

Example B2

Herbicidal Action

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days, the test was evaluated (10=total damage to plant; 0=no damage to plant).

TABLE B2

| | Application post-emergence | | | | |
|---|---|---|---|---|---|
| Comp No. | Rate (g/ha) | SOLNI | AMARE | SETFA | ECHCG | IPOHE |
| A9 | | 8 | 8 | 4 | 7 | 8 |
| A10 | | 9 | 9 | 6 | 7 | 8 |
| A11 | | 8 | 9 | 8 | 8 | 8 |
| A12 | | 10 | 9 | 8 | 8 | 9 |
| A13 | | 5 | 6 | 6 | 6 | 6 |
| A14 | | 7 | 5 | 7 | 6 | 4 |
| A15 | | 4 | 2 | 0 | 3 | 4 |
| A16 | | 9 | 10 | 6 | 6 | 7 |
| A18 | | 9 | 10 | 7 | 7 | 9 |
| A19 | | 10 | 10 | 4 | 6 | 8 |
| A21 | | 8 | 9 | 7 | 7 | 7 |

SOLNI = *Solanum nigrum*;
AMARE = *Amaranthus retroflexus*;
SETFA = *Setaria faberi*;
ECHCG = *Echinochloa crus-galli*;
IPOHE = *Ipomea hederaceae*.

The invention claimed is:
1. A compound of formula (Ib)

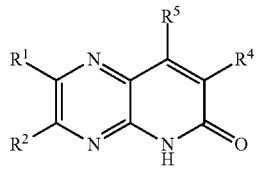

(Ib)

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^4$ is heteroaryl or heteroaryl substituted by one to four $R^8$, which may be the same or different; and
$R^5$ is $R^9$-oxy-, $R^{10}$-carbonyloxy-, tri-$R^{11}$-silyloxy- or $R^{12}$-sulfonyloxy-, wherein
$R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;
$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different;
each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy; each $R^6$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyl-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and each $R^{13}$ is independently halo, cyano, nitro, $C_1$-$C_6$alkyl, $C_1$-$C_6$haloalkyl or $C_1$-$C_6$alkoxy; or a herbicidally effective salt or N-oxide thereof.

2. A herbicidal composition which comprises a herbicidally effective amount of a compound of formula (Ib) as defined in claim 1 in addition to formulation adjuvants.

3. A compound of formula (Ic)

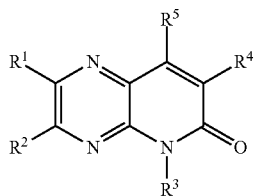

(Ic)

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;

$R^4$ is heteroaryl or heteroaryl substituted by one to four $R^8$, which may be the same or different;

$R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is $R^9$-oxy-, $R^{10}$-carbonyloxy-, tri-$R^{11}$-silyloxy- or $R^{12}$-sulfonyloxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;

$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different;

each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy; each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and each $R^{13}$ is independently halo, cyano, nitro, $C_1$-$C_6$alkyl, $C_1$-$C_6$haloalkyl or $C_1$-$C_6$alkoxy; or a herbicidally effective salt or N-oxide thereof.

4. A compound of formula (Id)

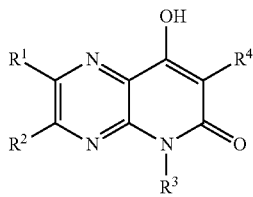

(Id)

wherein $R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;

$R^4$ is heteroaryl or heteroaryl substituted by one to four $R^8$, which may be the same or different; and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and each $R^{13}$ is independently halo, cyano, nitro, $C_1$-$C_6$alkyl, $C_1$-$C_6$haloalkyl or $C_1$-$C_6$alkoxy; or a herbicidally effective salt or N-oxide thereof.

\* \* \* \* \*